(12) United States Patent
Whitt et al.

(10) Patent No.: US 7,994,295 B2
(45) Date of Patent: Aug. 9, 2011

(54) RECOMBINANT VIRUSES COMPRISING THE MEMBRANE-PROXIMAL DOMAIN OF VSV G PROTEIN

(75) Inventors: Michael A. Whitt, Cordova, TN (US); Clinton S. Robison, Memphis, TN (US)

(73) Assignee: The University of Tennessee Research Corporation, Knoxville, TN (US)

( * ) Notice: Subject to any disclaimer, the term of this patent is extended or adjusted under 35 U.S.C. 154(b) by 1055 days.

(21) Appl. No.: 10/327,673

(22) Filed: Dec. 23, 2002

(65) Prior Publication Data

US 2010/0167377 A1      Jul. 1, 2010

Related U.S. Application Data

(63) Continuation-in-part of application No. 09/217,967, filed on Dec. 22, 1998, now Pat. No. 6,497,873.

(60) Provisional application No. 60/068,472, filed on Dec. 22, 1997.

(51) Int. Cl.
*C07H 21/04* (2006.01)
*C07K 14/47* (2006.01)

(52) U.S. Cl. ............ 536/23.1; 536/23.4; 536/23.5; 435/6; 435/325; 530/300; 514/2.2

(58) Field of Classification Search ................ None
See application file for complete search history.

(56) References Cited

U.S. PATENT DOCUMENTS 6,168,943 B1 * 1/2001 Rose ............................ 435/239
2002/0086356 A1   7/2002 Tuschl et al.

FOREIGN PATENT DOCUMENTS

WO   WO 03/092582   * 11/2003

OTHER PUBLICATIONS

Kretzschmar et al., J Virol, 1997, 71: 5982-5989.*
Schnell et al., Proc Natl. Acad. Sci USA, 1996, 93: 11359-11365.*
Mackett et al., Science, 1985, 227: 433-435.*
Li et al., J Virol, 1993, 67: 4070-4077.*
Schnell et al., Proc Nati Acad Sci USA, Oct. 1996, 93: 11359-11365.*
Rose et al., J Virol, 1981, 39: 519-528.*
Somia et al., Proc Natl Acad Sci USA, 1995, 92: 7570-7574.*
Lawson et al., Proc Natl Acad Sci USA, 1995, 92: 4477-4481.*
Schnell et al., J. Virol., 1996, 70: 2318-2323.*
U.S. Appl. No. 60/068,472, filed Apr. 2002, US, Kobinger et al.*
Berger, E. A., et al (1999) Chemokine receptors as HIV-1 coreceptors: roles in viral entry, tropism, and disease. Annu Rev Immunol. 17:657-700.
Blumenthal, R., et al (1987) pH-dependent fusion of vesicular stomatitis virus with Vero cells. Measurement by dequenching of octadecyl rhodamine fluorescence. J Biol Chem. 262:13614-13619.
Bricker B.J., et al (1987). Monoclonal antibodies to the glycoprotein of vesicular stomatitis virus (New Jersey serotype): A method for preliminary mapping of epitopes. Virology. 161:533-540.

Broder, C. C., et al (1993) The block to HIV-1 envelope glycoprotein-mediated membrane fusion in animal cells expressing human CD4 can be overcome by a human cell component(s). Virology. 1993:483-491.
Chernomordik, L., et al (1995) The hemifusion intermediate and its conversion to complete fusion: regulation by membrane composition. Biophys J. 69:922-929.
Cathomen, T. et al (1998) Measles viruses with altered envelope protein cytoplasmic tails gain cell fusion competence. J. Virol. 72: 1224-1234.
Chu T. H. T et al (1997) Toward highly efficient cell-type-specific gene transfer with retroviral vectors displaying single-chain antibodies, Journal of Virology, vol. 71, No. 1, pp. 720-725.
Dolter K. E. et al (1993) Incorporation of CD4 into Virions by a Recombinant Herpes Simplex Virus, Journal of Virology, vol. 67, No. 1 pp. 189-195.
Doms, R. W., et al (2000) HIV-1 membrane fusion: targets of opportunity. J Cell Biol. 151:9-14.
Durrer, P., et al (1995) Photolabeling identifies a putative fusion domain in the envelope glycoprotein of rabies and vesicular stomatitis viruses. J. Biol. Chem. 270:17575-17581.
Fan, D. P., et al (1978) The entry into host cells of Sindbis virus, vesicular stomatitis virus, and Sendai virus. Cell. 15:985-992.
Feng, Y., et al (1996) HIV-1 entry cofactor: functional cDNA cloning of a seven-transmembrane, G protein-coupled receptor. Science. 272:872-877.
Florkiewicz, R. Z., et al (1984) A cell line expressing vesicular stomatitis virus glycoprotein fuses at low pH. Science. 225:721-723.
Fredericksen, B. L., et al (1998) Attenuation of recombinant vesicular stomatitis viruses encoding mutant glycoproteins demonstrates a critical role for maintaining a high pH threshold for membrane fusion in viral fitness. Virology. 240:349-358.
Fredericksen, B. L., et al (1996) Mutations at two conserved acidic amino acids in the glycoprotein of vesicular stomatitis virus affect pH-dependent conformational changes and reduce the pH threshold for membrane fusion. Virology. 217:49-57.
Fredericksen, B. L., et al (1995) Vesicular stomatitis virus glycoprotein mutations that affect membrane fusion activity and abolish virus infectivity. J Virol. 69:1435-1443.
Fuerst, T. R. et al (1987) Use of a hybrid vaccinia virus-T7 RNA polymerase system for expression of target genes. Mol Cell Biol. 7:2538-2544.
Gaudin, Y., et al (1996) Identification of amino acids controlling the low-pH-induced conformational change of rabies virus glycoprotein. J. Virol. 70:7371-7378.
Galmiche M.C. et al (1997) Expression of a functional single chain antibody on the surface of extracellular enveloped vaccinia virus as a step towards selective tumour cell targeting.
Helenius, A. (1993) Influenza virus fusion: From models towards a mechanism. p. 89-111. In J. Bentz (ed.), Viral fusion mechanisms, vol. 1. CRC press, Ann Arbor.
Horvath, C. M., et al (1992) Biological activity of paramyxovirus fusion proteins: factors influencing formation of syncytia. J. Virol. 66:4564-4569.

(Continued)

*Primary Examiner* — James D. (Doug) Schultz
(74) *Attorney, Agent, or Firm* — Pearl Cohen Zedek Latzer, LLP; Mark S. Cohen

(57) ABSTRACT

Recombinant viruses, isolated nucleic acids and methods of generating same encoding for a Rhabdoviral G stem polypeptide are disclosed. Methods, compounds and compositions for target cell fusion potentiation mediated by Rhabdoviral G stem polypeptides, and applications of same are provided.

10 Claims, 9 Drawing Sheets

OTHER PUBLICATIONS

Figure 1:
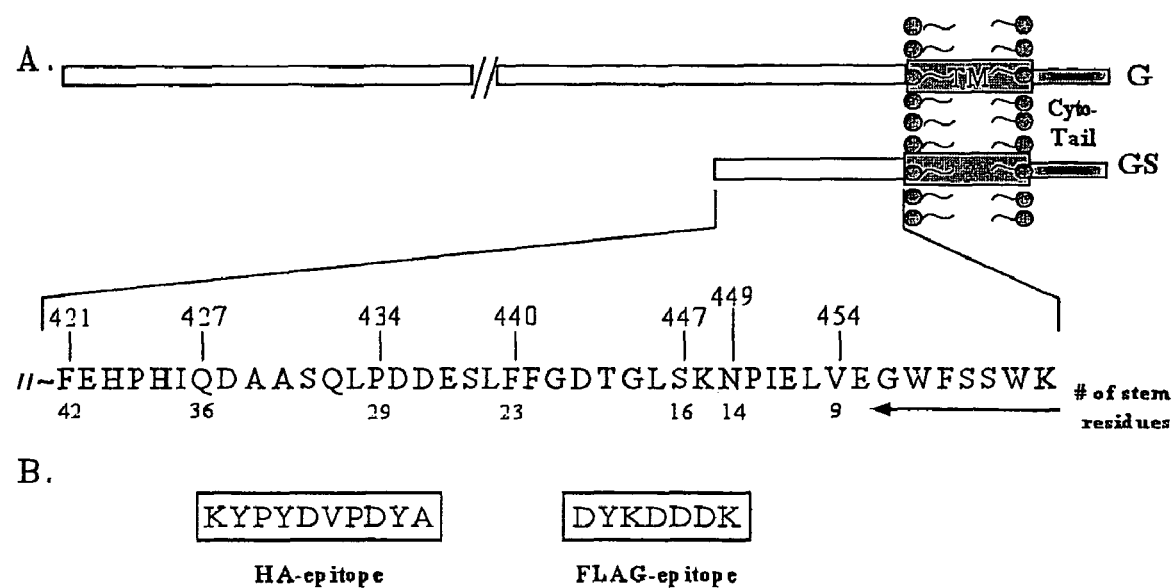

Jayakar, H. R., et al (2000) Mutations in the PPPY motif of vesicular stomatitis virus matrix protein reduce virus budding by inhibiting a late step in virion release. J Virol. 74:9818-9827.

Jeetendra, E. et al (2001) Characterization of the minimal budding domain in the vesicular stomatitis virus (VSV) glycoprotein, p. 96: W19-2. 20th Annual Meeting of the American Society for Virology, University of Wisconsin-Madison, Madison, Wisconsin.

Johnson J. E. (1997) Specific targeting to CD4+ Cells of Recombinant Vesicular Stomatitis Viruses Encoding Human Immunodeficiency Virus Envelope Proteins, Journal of Virology, vol. 7 No. 7, pp. 5060-5068.

Kuzmin, P. I. et al (2001) A quantitative model for membrane fusion based on low-energy intermediates. Proc Natl Acad Sci U S A. 98:7235-7240.

Kreis, T. E., et al (1986) Oligomerization is essential for transport of vesicular stomatitis virus glycoprotein to the cell surface. Cell. 46:929-937.

Lamb R. A. (1993) Mini review: Paramyxovirus Fusion: A Hypothesis for Changes, Virology 197, 1-11.

Lawson, N., et al (1995) Recombinant vesicular stomatitis viruses from DNA. Proc. Natl. Acad. Sci. (USA). 92:4477-4481.

Lefrancois, L., et al (1982) The interaction of antibody with the major surface glycoprotein of vesicular stomatitis virus. I. Analysis of neutralizing epitopes with monoclonal antibodies. Virology. 121:157-167.

Li, Y., C. Drone, E. Sat, and H. P. Ghosh. 1993. Mutational analysis of the vesicular stomatitis virus glycoprotein G for membrane fusion domains. J. Virol. 67:4070-4077.

Marin M, et al (1996) Targeted Infection of Human Cells vi9a Major Histocompatibility Complex Class I Molecules by Moloney Murine Leukemia Virus-Derived Viruses Displaying Single-Chain Antibody Fragment-Envelope Fusion Proteins, Journal of Virology, vol. 70, No. 5, pp. 2957-2962.

Marsh, M., et al (1989) Virus entry into animal cells. Adv. Virus Res. 36:107-151.

Matsushita, S., et al (1988) Characterization of a human immunodeficiency virus neutralizing monoclonal antibody and mapping of the neutralizing epitope. J Virol. 62:2107-2114.

McCallus, D. E., et al (1992) Construction of a recombinant bacterial human CD4 expression system producing a bioactive CD4 molecule. Viral Immunol. 5:163-172.

Mebatsion T. et al (1996) Budding of Rabies Virus Particles in the Absence of the Spike Glycoprotein, Cell, vol. 84, pp. 941-951.

Mebatsion T. et al (1996) Specific Infection of CD4+ target cells by recombinant rabies virus pseudotypes carrying the HIV-1 envelope spike protein, Proc. Natl. Acad. Sci. Vo. 93, pp. 11366-11370.

Mebatsion T. et al (1997) A CXCR4/CD4 Pseudotype Rhabdovirus that selectively infects HIV-1 Envelope Protein-Expressing Cells, Cell, vol. 90, pp. 841-847.

Melikyan, G. B., et al (1997) Inner but not outer membrane leaflets control the transition from glycosylphosphatidylinositol-anchored influenza hemagglutinin-induced hemifusion to full fusion. J Cell Biol. 136:995-1005.

Munoz-Barroso, I. et al (1999) Role of the membrane-proximal domain in the initial stages of human immunodeficiency virus type 1 envelope glycoprotein-mediated membrane fusion. J Virol. 73:6089-6092.

Munoz-Barroso, I., et al (1998) Dilation of the human immunodeficiency virus-1 envelope glycoprotein fusion pore revealed by the inhibitory action of a synthetic peptide from gp41. J Cell Biol. 140:315-323.

Niwa, H., et al (1991) Efficient selection for high-expression transfectants with a novel eukaryotic vector. Gene. 108:193-199.

Nolan G. P. (1997) Harnessing viral devices as Pharmaceuticals: fighting HIV01's Fire with Fire, Cell. vol. 90, pp. 821-824.

Ohnishi, S. (1988) Fusion of viral envelopes with cellular membranes. Curr. Topics in Membranes and Transport. 32:257-298.

Oravecz, T., et al (1993) Costimulatory properties of the human CD4 molecule: enhancement of CD3-induced T cell activation by human immunodeficiency virus type 1 through viral envelope glycoprotein gp120. AIDS Res Hum Retroviruses. 9:945-955.

Paternostre, M. T et al (1989) pH-dependent fusion of reconstituted vesicular stomatitis virus envelopes with Vero cells. Measurement by dequenching of fluorescence. FEBS Lett. 243:251-258.

Paterson, R. G., et al (1985) Expression at the cell surface of biologically active fusion and hemagglutinin/neuraminidase proteins of the paramyxovirus simian virus 5 from cloned cDNA. Proc Natl Acad Sci U S A. 82:7520-7524.

Pattnaik A.K. et al (1992) Infectious Defective Interfering Particles of VSV from Transcripts of a cDNA Clone, Cell. vol. 69, 1011-1020.

Pattnaik A.K. et al (1991) Cells that express all five proteins of vesicular stomatitis virus from cloned cDNAs support replication, assembly, and budding of defective interfering particles, Proc. Natl. Acad. Sci. vol. 88, pp. 1379-1383.

Ratner, L., et al (1985) Complete nucleotide sequence of the AIDS virus, HTLV-III. Nature. 313:277-284.

Roberts, P. C., et al (1999) Vesicular stomatitis virus G protein acquires pH-independent fusion activity during transport in a polarized endometrial cell line. J Virol. 73:10447-10457.

Robison, C. S., et al (2000) The membrane-proximal stem region of vesicular stomatitis virus G protein confers efficient virus assembly J Virol. 74:2239-2246.

Rose, J. K., et al (1991) A new cationic liposome reagent mediating nearly quantitative transfection of animal cells. BioTechniques. 10:520-525.

Pattnaik A.K. et al (1990) Replication and Amplification of Defective Interfering Particle RNAs of Vesicular Stomatitis Virus in Cells Expressing Viral Proteins from Vectors Containing Cloned cDNAs, Journal of Virology, vol. 64, No. 6, pp. 2948-2957.

Puri, A., et al (1993) A new approach to measure fusion activity of cloned viral envelope proteins: fluorescence dequenching of octadecylrhodamine-labeled plasma membrane vesicles fusing with cells expressing vesicular stomatitis virus glycoprotein. Virology. 195:855-858.

Randall, R. E., et al (1987) Isolation and characterization of monoclonal antibodies to simian virus 5 and their use in revealing antigenic differences between human, canine and simian isolates. J Gen Virol. 68:2769-2780.

Salzwedel, K., et al (1999) A conserved tryptophan-rich motif in the membrane-proximal region of the human immunodeficiency virus type 1 gp41 ectodomain is important for Env-mediated fusion and virus infectivity. J Virol. 73:2469-2480.

Schnell, M. J., (1997) Construction of a novel virus that targets HIV-1-infected cells and controls HIV-1 infection. Cell. 90:849-857.

Schnell M.J. et al (1996) Foreign glycoproteins expressed from recombinant vesicular stomatitis viruses are incorporated efficiently into virus particulars, Proc. Natl. Acad. Sci. vol. 93, pp. 11359-11365.

Schnell, M J. et al (1994) Infectious rabies viruses from cloned cDNA, The EMBO Journal, vol. 13, No. 18 pp. 4195-4203.

Shokralla, S., et al (1999) Effects of double-site mutations of vesicular stomatitis virus glycoprotein G on membrane fusion activity. Virology. 256:119-129.

Shokralla, S., et al (1998) Mutations in a carboxy-terminal region of vesicular stomatitis virus glycoprotein G that affect membrane fusion activity. Virology. 242:39-50.

Stillman E. A. (1995) Replication and Amplification of Novel Vesicular Stomatitis Virus Minigenomes Encoding Viral Structural Proteins, Journal of Virology, vol. 69, No. 5, pp. 2946-2953.

Suarez, T., et al (2000) Membrane interface interacting sequences within the ectodomain of the human immunodeficiency virus type 1 envelope glycoprotein: putative role during viral fusion. J Virol. 74:8038-8047.

Takada, A., et al (1997) A system for functional analysis of Ebola virus glycoprotein. Proc Natl Acad Sci U S A. 94:14764-14769.

Tong, S., et al (2001) Three membrane-proximal amino acids in the human parainfluenza type 2 (HPIV 2) F protein are critical for fusogenic activity. Virology. 280:52-61.

Wertz G. W. et al (1994) Extent of terminal complementarity modulates the balance between transcription and replication of vesicular stomatitis virus RNA, Proc. Natl. Acad. Sci. vol. 91, pp. 8587-8594.

Whelan S.P.J. (1995) Efficient recovery of infectious vesicular stomatitis virus entirely from cDNA clones, Proc. Natl. Acad. Sci. vol. 92, pp. 8388-8392.

White, J. M. (1990) Viral and cellular membrane fusion proteins. Annu. Rev. Physiol. 52:675-697.

Whitt, M. A., et al (1991) TransfectACE Reagent: Transient transfection frequencies greater than 90%. Focus. 13:8-12.

Whitt, M. A., et al (1990) A fusion-defective mutant of the vesicular stomatitis virus glycoprotein. J Virol. 64:4907-4913.

Yang F., et al (1994) Monoclonal antibody to the C-terminus of β-amyloid, NeuroReport 5, 2117-2120.

Young J. A. T. et al (1990) Efficient Incorporation of Human CD4 Protein into Avian Leukosis Virus Particles, Science, vol. 250, pp. 1421-1423.

Zhang, L., et al (1994) Characterization of the putative fusogenic domain in vesicular stomatitis virus glycoprotein G. J. Virol. 68:2186-2193.

Zhou, J., R. E. Dutch, and R. A. Lamb. 1997. Proper spacing between heptad repeat B and the transmembrane domain boundary of the paramyxovirus SV5 F protein is critical for biological activity. Virology. 239:327-339.

* cited by examiner

A                        B

SV5 F             SV5 F + GS (co-txn)

SEQUENCE LISTING

<160> NUMBER OF SEQ ID NOS: 15

<210> SEQ ID NO 1
<211> LENGTH: 273
<212> TYPE: DNA
<213> ORGANISM: Vesicular stomatitis virus

<400> SEQUENCE: 1

```
ttcgaacatc ctcacattca agacgctgct tcgcaacttc ctgatgatga gagtttattt      60
tttggtgata ctgggctatc caaaaatcca atcgagcttg tagaaggttg gttcagtagt     120
tggaaaagct ctattgcctc ttttttcttt atcatagggt taatcattgg actattcttg     180
gttctccgag ttggtatcca tctttgcatt aaattaaagc acaccaagaa aagacagatt     240
tatacagaca tagagatgaa ccgacttgga aag                                  273
```

<210> SEQ ID NO 2
<211> LENGTH: 91
<212> TYPE: PRT
<213> ORGANISM: Vesicular stomatitis virus

<400> SEQUENCE: 2

```
Phe Glu His Pro His Ile Gln Asp Ala Ala Ser Gln Leu Pro Asp Asp
1               5                   10                  15
```

```
Glu Ser Leu Phe Phe Gly Asp Thr Gly Leu Ser Lys Asn Pro Ile Glu
        20                  25                  30

Leu Val Glu Gly Trp Phe Ser Ser Trp Lys Ser Ser Ile Ala Ser Phe
        35                  40                  45

Phe Phe Ile Ile Gly Leu Ile Ile Gly Leu Phe Leu Val Leu Arg Val
50                  55                  60

Gly Ile His Leu Cys Ile Lys Leu Lys His Thr Lys Lys Arg Gln Ile
65                  70                  75                  80

Tyr Thr Asp Ile Glu Met Asn Arg Leu Gly Lys
                85                  90

<210> SEQ ID NO 3
<211> LENGTH: 9
<212> TYPE: PRT
<213> ORGANISM: Vesicular stomatitis virus

<400> SEQUENCE: 3

Val Glu Gly Trp Phe Ser Ser Trp Lys
1               5

<210> SEQ ID NO 4
<211> LENGTH: 14
<212> TYPE: PRT
<213> ORGANISM: Vesicular stomatitis virus

<400> SEQUENCE: 4

Asn Pro Ile Glu Leu Val Glu Gly Trp Phe Ser Ser Trp Lys
1               5                   10

<210> SEQ ID NO 5
<211> LENGTH: 16
<212> TYPE: PRT
<213> ORGANISM: Vesicular stomatitis virus

<400> SEQUENCE: 5

Ser Lys Asn Pro Ile Glu Leu Val Glu Gly Trp Phe Ser Ser Trp Lys
1               5                   10                  15

<210> SEQ ID NO 6
<211> LENGTH: 23
<212> TYPE: PRT
<213> ORGANISM: Vesicular stomatitis virus

<400> SEQUENCE: 6

Phe Phe Gly Asp Thr Gly Leu Ser Lys Asn Pro Ile Glu Leu Val Glu
1               5                   10                  15

Gly Trp Phe Ser Ser Trp Lys
            20

<210> SEQ ID NO 7
<211> LENGTH: 29
<212> TYPE: PRT
<213> ORGANISM: Vesicular stomatitis virus

<400> SEQUENCE: 7

Pro Asp Asp Glu Ser Leu Phe Phe Gly Asp Thr Gly Leu Ser Lys Asn
1               5                   10                  15

Pro Ile Glu Leu Val Glu Gly Trp Phe Ser Ser Trp Lys
            20                  25

<210> SEQ ID NO 8
<211> LENGTH: 36
```

```
<212> TYPE: PRT
<213> ORGANISM: Vesicular stomatitis virus

<400> SEQUENCE: 8

Gln Asp Ala Ala Ser Gln Leu Pro Asp Asp Glu Ser Leu Phe Phe Gly
1               5                   10                  15

Asp Thr Gly Leu Ser Lys Asn Pro Ile Glu Leu Val Glu Gly Trp Phe
            20                  25                  30

Ser Ser Trp Lys
        35

<210> SEQ ID NO 9
<211> LENGTH: 42
<212> TYPE: PRT
<213> ORGANISM: Vesicular stomatitis virus

<400> SEQUENCE: 9

Phe Glu His Pro His Ile Gln Asp Ala Ala Ser Gln Leu Pro Asp Asp
1               5                   10                  15

Glu Ser Leu Phe Phe Gly Asp Thr Gly Leu Ser Lys Asn Pro Ile Glu
            20                  25                  30

Leu Val Glu Gly Trp Phe Ser Ser Trp Lys
        35                  40

<210> SEQ ID NO 10
<211> LENGTH: 39
<212> TYPE: DNA
<213> ORGANISM: Vesicular stomatitis virus

<400> SEQUENCE: 10
aggatgaccc gagccagcgt aatctggtac atcatacgg                          39

<210> SEQ ID NO 11
<211> LENGTH: 56
<212> TYPE: DNA
<213> ORGANISM: Vesicular stomatitis virus

<400> SEQUENCE: 11
gacccgagcc cttatcgtca tcatctttgt agtcgaactt gcaattcacc ccaatg       56

<210> SEQ ID NO 12
<211> LENGTH: 38
<212> TYPE: DNA
<213> ORGANISM: Vesicular stomatitis virus

<400> SEQUENCE: 12
ccaaacatga agcttctgtt gtgcatgctt tgagttac                           38

<210> SEQ ID NO 13
<211> LENGTH: 12
<212> TYPE: DNA
<213> ORGANISM: Vesicular stomatitis virus

<400> SEQUENCE: 13
atggcctcgg gt                                                       12

<210> SEQ ID NO 14
<211> LENGTH: 17
<212> TYPE: DNA
<213> ORGANISM: Vesicular stomatitis virus

<400> SEQUENCE: 14
tggatggagt gggacag                                                  17
```

```
<210> SEQ ID NO 15
<211> LENGTH: 38
<212> TYPE: DNA
<213> ORGANISM: Vesicular stomatitis virus

<400> SEQUENCE: 15
gttatacccg agatattcca caaacttgcc catttatc                              38
```

RECOMBINANT VIRUSES COMPRISING THE MEMBRANE-PROXIMAL DOMAIN OF VSV G PROTEIN

This application is a Continuation-in-part Application of U.S. application Ser. No. 09/217,967, filed Dec. 22, 1998 now U.S. Pat. No. 6,497,873, which claims priority of Provisional Application No. 60/068,472, filed Dec. 22, 1997, which are incorporated herein by reference.

FIELD OF THE INVENTION

The present invention relates to a recombinant Rhabdovirus and methods of generating same comprising a deletion in a nucleic acid sequence encoding a Rhabdoviral G protein with an insertion of a nucleic acid encoding a Rhabdoviral G stem polypeptide within a region of the G protein. Furthermore, the recombinant Rhabdovirus of the present invention is capable of expressing foreign nucleic acids within their genome.

BACKGROUND OF THE INVENTION

Rhabdoviridae are membrane-enveloped viruses that are widely distributed in nature where they infect vertebrates, invertebrates, and plants. The Rhabdoviridae are divided into 6 genera, wherein Vesicular stomatitis virus (VSV) serves as a prototype for the vesiculovirus genus. Rhabdoviridae possess non-segmented, negative-strand RNA genomes of 11-12,000 nucleotides. The virus particles contain a helical, nucleocapsid core composed of the genomic RNA and protein. Generally, three proteins, termed N (nucleocapsid, which encases the genome tightly), P (formerly termed NS, originally indicating nonstructural), and L (large) are found to be associated with the nucleocapsid. An additional matrix (M) protein lies within the membrane envelope, perhaps interacting both with the membrane and the nucleocapsid core. A single glycoprotein (G) species spans the membrane and forms the spikes on the surface of the virus particle. The G protein is responsible for binding to host cells and facilitating membrane fusion. Because the Rhabdoviral genome is negative sense [i.e., complementary to host cell RNA sequences (positive sense) that comprise host mRNA], for transcription and translation of Rhabdoviral genes to occur, the virus must encode and package an RNA-dependent RNA polymerase in its virion. The RNA-dependant RNA polymerase is composed of the P and L proteins, which transcribes genomic RNA to subgenomic mRNA's encoding the 5-6 Rhabdoviral proteins and also replicates full-length positive and negative sense RNAs. Rhabdoviral genes are transcribed sequentially, starting at the 3' end of the genome.

Due to its broad host range, simple genetic organization and rapid growth in cell culture, VSV has been used widely to study various aspects of Rhabdoviral entry, assembly and release. The virus enters cells via receptor-mediated endocytosis. Approximately 1200 VSV glycoprotein (G) molecules, organized as homotrimeric spikes anchored in the viral envelope, are responsible for virus attachment as well as for mediating fusion of the viral envelope with the endosomal membrane of the host cell following endocytosis. Low endosomal pH causes a conformational change in the G protein facilitating fusion of the viral envelope with the endosomal membrane (9, 2, 26). Fusion of the two membranes results in the release of the viral nucleocapsid into the host cell cytoplasm where viral replication then occurs.

VSV G protein differs from the prototypic viral fusion protein, influenza hemagglutinin (HA), in that G protein does not require proteolytic processing to become fusion-competent (33, 17). Also unlike influenza HA, the N-terminus of G, apart from the signal sequence, is not particularly hydrophobic and there is no obvious region in the amino acid sequence that can be defined as a "classical" fusion peptide (51). It was postulated that the VSV G fusion peptide is internal and that the region between amino acids (aa) 118-139 could be the putative fusion domain (33). Mutational analysis has provided evidence that the region between aa 118-136 corresponds to the G protein fusion peptide (14, 25, 53, 55).

Other regions of G protein have also been shown to be important for its fusion activity. Insertion of a 3 aa linker in the membrane-proximal domain at positions 410 and 415 abolished membrane fusion activity, indicating that this region may be important for fusion (25). Substitution of amino acids in the region between 395 and 418 also affected the fusogenic activity of G protein (47). When mutations in the fusion peptide were combined with point mutations in the membrane-proximal region between amino acids 395-418 fusion activity was inhibited additively. However, one double mutant G131A-G404A was more fusogenic than the two individual mutations alone, suggesting that these regions may interact during fusion (46).

The membrane proximal region of the VSV G protein is highly conserved among vesiculovirus members (41). Structure predictions for the region between aa 385 and 444 of the VSV GIND serotype glycoprotein have indicated that this region has a propensity to form α-helices suggestive of its direct interaction with cellular membranes (16). Recently the Applicants have demonstrated that the membrane proximal ectodomain of the "stem" region of the VSV G protein (G-stem or GS) is responsible for efficient VSV budding (41), a finding which may perhaps be technically exploited for the development of the next generation of recombinant VSV vectors. There is, therefore, an advantage in developing recombinant VSV vectors containing the membrane proximal "stem" region of the VSV G protein ectodomain as these may provide accelerated fusion activity, a result providing a multiple of biologically relevant applications.

SUMMARY OF INVENTION

In one embodiment, the present invention relates to a recombinant Rhabdovirus and methods of generating same. The recombinant Rhabdovirus comprises a deletion in a nucleic acid sequence encoding a Rhabdoviral G protein with an insertion of a nucleic acid encoding for a fragment of a Rhabdoviral G stem polypeptide within a region of the G protein. Specifically, the present invention relates to recombinant Rhabdoviruses expressing G stem polypeptides lacking significant portions of the G protein, potentiating their fusion with target cell membranes. Fusion is potentiated by the incorporation of a heterologous fusion facilitating polypeptide, and further still with the incorporation of an anti-receptor, which aids in specific targeting of the recombinant Rhabdovirus to a given cell type. The invention relates to isolated nucleic acids comprising the components as delineated above, including nucleic acid vectors comprising the isolated nucleic acids, and cells comprising the sequences and/or vectors.

In another embodiment of the present invention, there is provided a recombinant Rhabdovirus comprising a nucleic acid sequence of a Rhabdoviral genome, wherein the Rhabdoviral genome comprises a deletion in the nucleic acid sequence encoding a Rhabdoviral G protein, and an insertion in a nucleic acid sequence encoding a Rhabdoviral G stem polypeptide, or fragment thereof.

In another embodiment, the recombinant Rhabdovirus further comprises a nucleic acid, which encodes for a fusion-facilitating polypeptide, or fragment thereof, which may be expressed from a separate transcriptional unit. The fusion facilitating polypeptide may be derived from a simian virus 5 F protein, or an HIV envelope protein.

In another embodiment, the recombinant Rhabdovirus lacks amino acids 1 to 404 of the mature G protein.

In another embodiment, the recombinant Rhabdovirus encodes for a G stem polypeptide, or fragment thereof that comprises between at least 10 and 42 amino acid residues of a membrane-proximal region of a Rhabdoviral G protein. The G stem polypeptide may also comprise a transmembrane anchor and cytoplasmic tail region of a Rhabdoviral G protein. The encoded G stem polypeptide or fragment thereof may be further engineered to express an N-terminal epitope tag, of which c-myc, FLAG®, human influenza hemagglutinin (HA) or polyhistidine (including His6 or His 10) tags may be utilized.

In another embodiment, the nucleic acid sequence encoding a Rhabdoviral G stem polypeptide, or fragment thereof corresponds to or is at least 70%, at least 75%, at least 80%, at least 85%, at least 90%, at least 95% or more, including 95%-100% homologous to SEQ ID No: 1. The encoded Rhabdoviral G stem polypeptide or fragment thereof, in turn corresponds to or is at least 70%, at least 75%, at least 80%, at least 85%, at least 90%, at least 95% or more, including 95%-100% homologous to SEQ ID Nos: 2, 4, 5, 6, 7, 8 or 9.

In yet another embodiment, the recombinant Rhabdovirus may further comprise an insertion of a heterologous nucleic acid sequence encoding for a second polypeptide. The second polypeptide may function as a receptor that specifically binds a cognate ligand on a target cell membrane functioning in targeting the recombinant Rhabdovirus to a given host cell. In another embodiment, the stated polypeptide may comprise a ligand for binding to specific target cell receptors. Such ligands are also referred to as "anti-receptor" proteins and may comprise polypeptide fragments thereof, uncompromised in their targeting ability. The anti-receptor proteins may comprise antibodies or antibody fragments that recognize a target antigen, such as for example CD4, or erbB proteins expressed on target cell membranes. Other cell surface proteins used for targeting the recombinant Rhabdoviruses of the invention may include chemokine receptors, adhesion molecule receptors, MHC molecules, and others, all of which may be similarly applied.

In another embodiment, there is provided a recombinant virus comprising a nucleic acid sequence encoding for a Rhabdoviral G stem polypeptide, or fragment thereof. The Rhabdoviral G stem polypeptide may comprise between at least 10 and 42 amino acid residues of a membrane-proximal region, a transmembrane anchor and cytoplasmic tail region of a Rhabdoviral G protein, and/or be further engineered to express an N-terminal epitope tag, The Rhabdoviral G stem polypeptide will correspond to, or exhibit similar homology to sequences listed hereinabove.

The recombinant virus, may, according to another aspect of the invention, further comprise a nucleic acid sequence encoding for a fusion facilitating polypeptide. In other embodiments, the recombinant virus further comprises an insertion of a non-Rhabdoviral nucleic acid sequence, which may function as a receptor that specifically binds a cognate ligand on a target cell membrane to facilitate targeting the recombinant virus to a given host cell. In another embodiment, the nucleic acid sequence may comprise a ligand for binding to specific target cell receptors. Such ligands are also referred to as "anti-receptor" proteins and may comprise polypeptide fragments thereof, uncompromised in their targeting ability.

In another embodiment of the present invention, vectors comprising the recombinant Rhabdoviruses or recombinant viruses, and cells comprising these vectors are included. Viral particles and/or liposomes comprising the recombinant Rhabdoviruses or recombinant viruses are additional applications of the present invention.

The present invention provides for a method of fusing a cell with the recombinant Rhabdoviruses or recombinant viruses or cells expressing the viral products. The to method comprises contacting a cell with the recombinant Rhabdovirus, or recombinant virus, under conditions facilitating fusion of the viral envelope or outer cell membrane with a lipid bilayer of a target cell. In another embodiment, a method of fusing viral particles comprising recombinant Rhabdoviruses or recombinant viruses with a target cell is provided, the method as described herein.

The present invention further provides for a method of potentiating cell fusion, comprising the step of contacting a cell with a recombinant Rhabdovirus or recombinant virus, wherein the recombinant Rhabdovirus or recombinant virus expresses a heterologous fusion facilitating peptide, and a G stem polypeptide, under conditions facilitating fusion of the Rhabdoviral envelope with the lipid bilayer membrane of a target cell, resulting in potentiated fusion. In another embodiment, the method of potentiating cell fusion if via contacting a cell with a cell expressing the recombinant Rhabdovirus, or recombinant virus as described herein.

The present invention further provides a method of producing a recombinant Rhabdovirus comprising a deletion in the nucleic acid sequence encoding the Rhabdoviral G protein and an insertion of a nucleic acid sequence encoding a Rhabdoviral G stem polypeptide fragment and a nucleic acid sequence encoding a heterologous fusion facilitating polypeptide, the method comprising the steps of: (A) infecting a suitable cell with a minivirus comprising the cis-acting elements necessary for Rhabdoviral replication; (B) inserting into said cell a polynucleotide sequence encoding Rhabdoviral proteins, a nucleic acid sequence encoding a Rhabdoviral G stem polypeptide or a fragment thereof and a nucleic acid sequence encoding a heterologous fusion facilitating polypeptide; (C) culturing said cell under conditions that permit expression of the nucleic acid sequence to produce the recombinant Rhabdovirus; and (D) isolating said recombinant Rhabdovirus.

In another embodiment, there is provided an isolated nucleic acid molecule comprising a nucleic acid sequence encoding for a Rhabdoviral G stem polypeptide, or a fragment thereof, corresponding to or at least 70%, at least 75%, at least 80%, at least 85%, at least 90%, at least 95% or more, including 95%-100% homologous to SEQ ID Nos: 2, 4, 5, 6, 7, 8 or 9. The G stem polypeptide, or fragment thereof comprises between at least 10 and 42 amino acid residues of a membrane-proximal region of a Rhabdoviral G protein, and comprises a transmembrane anchor and cytoplasmic tail region of a Rhabdoviral G protein. The Rhabdoviral G stem polypeptide or fragment thereof may further comprise an N-terminal epitope tag, of which the FLAG synthetic or human influenza hemagglutining-derived polypeptide tags may be utilized.

In another embodiment, the isolated nucleic acid further comprises a nucleic acid sequence encoding for a fusion facilitating peptide. The isolated nucleic acid, may according to another embodiment, comprise a nucleic acid encoding for an anti-receptor protein or a polypeptide fragment thereof, as described herein, and may additionally comprise other non-Rhabdoviral nucleic acid sequences.

The invention provides, in another embodiment, a method of targeted cell lysis. The method comprises contacting a cell with an effective amount of a recombinant Rhabdovirus comprising a deletion in the nucleic acid sequence encoding a Rhabdoviral G protein, an insertion of a nucleic acid sequence encoding a Rhabdoviral G stem polypeptide, an insertion of a nucleic acid sequence encoding a heterologous fusion facilitating polypeptide, and an insertion of a nucleic acid sequence encoding an anti-receptor protein. In one embodiment of this aspect of the invention, following binding of the expressed anti-receptor to its cognate ligand or receptor on a target cell, the recombinant Rhabdovirus fuses with the target cell surface, facilitating viral entry, and subsequent target cell lysis.

BRIEF DESCRIPTION OF THE DRAWINGS

FIG. 1 is a schematic representation of GS truncations. A) The amino acid sequence of the membrane proximal ectodomain of G-protein is shown. The numbers at the top of the sequence indicate the positions of the amino acids from the N-terminus of G protein and correspond to the residues at which successive truncations of GS were made. The numbers below the sequence denote the number of amino acids from the transmembrane (TM) domain (box). B) The amino acid sequences of the hemagglutinin (HA) and FLAG epitopes that were used to tag the various GS truncations are shown.

FIG. 2 demonstrates the GS enhancement of membrane fusion induced by GNJ. BHK-21 cells were transfected with plasmids encoding for GSHA (A), GSHA and GNJ (B), or GNJ alone (C). At 36 hours post-transfection, cells were fixed with 3% paraformaldehyde and stained. The cells were not pretreated with fusion medium therefore, the pH was maintained at 7.2 to 7.4 throughout the incubation period. Cells expressing GNJ and GNJ+GSHA were probed with mAb VIII, which is specific for the GNJ glycoprotein. Cells expressing GSHA were stained with the 12CA5 mAb specific for the HA epitope. Representative epifluorescence and phase-contrast micrographs of the cells are shown.

FIG. 3 demonstrates the effect of GS on SV5 F-mediated membrane fusion. BHK-21 cells were transfected with plasmids encoding SV5 F alone or that were co-transfected with plasmids encoding SV5 F and GSHA. Cells were fixed with 3% paraformaldehyde at 36 hours after transfection and stained for surface expression of SV5 F using the monoclonal Fla, which is specific for F protein. Panel A shows the fusion activity of SV5 F alone. Panel B shows syncytia formation when SV5 F and GSHA are co-expressed.

FIG. 4 demonstrates that GS can function with HIV-1 Env to induce membrane fusion in a chemokine independent manner. (A) BHK-21 cells were transfected with plasmids encoding either gp160W3IGS alone, CD4 and GSHA together, the chimeric protein CD4-GS alone or GSHA alone. At 24 hours post-transfection the cells were removed from the plates divided into two aliquots and then replated. After an additional 24 hours the HIV-1 Env expressing cells were stained using the gp160-specific goat sera HT3. Cells expressing CD4 or CD4-GS were stained with the CD4 specific mAb Sim.2. Cells expressing GSHA were stained with an HA epitope-specific mAb. (B) After 24 hours of transfection the cells expressing CD4 only, GSHA only, CD4 and GSHA together, or CD4-GS were mixed with cells expressing gp160W3IGS and replated. The mixed cultures were incubated for an additional 24 hours, then fixed, processed and probed with the Sim.2 mAb for CD4 expression or for GSHA using mAb HA.11.

FIG. 5 demonstrates the binding of wild type VSV and GSHA virus to cells. Radiolabeled virions (~80,000 cpm) were resuspended in binding media adjusted to pH 7.0 or pH 5.9. The virus suspensions were added to cells and allowed to bind for 3 hours on ice. The inoculum was removed (unbound fraction) and the cells were washed three times with ice-cold binding media at the same pH to remove unbound virus. Cells were then solubilized with PBS containing 1% TX-100 and the lysates were collected (bound fraction). The amount of radioactivity in the bound and unbound fractions was determined by scintillation counting. The binding activity of the viruses is shown as a percentage of the total amount of input virus. Each bar represents an average of three separate experiments done in triplicate. ( —WT-VSV,  —GSHA virus,  —ΔG virus)

FIG. 6 demonstrates a three-color fusion assay. BRK-21 cells were infected with WT VSV (panels A and B), GSHA virus (panel C), or ΔG virus (panel D) at an MOI=10. After 8 hours of infection the cells were labeled with DiI (red) and calcein-AM (green) and then removed from the plates. The cells were then overlayered on BHK-21 cells that were previously labeled with CMAC (blue). After the virus-infected donor cells had attached to the plate or had settled onto the target cells, the medium was replaced with fusion media buffered to pH 5.9 or 7.0. After 1 minute the fusion buffer was removed and the cells were incubated for 20 minutes in growth medium at 37° C. and then placed on ice to prevent any further lipid or contents mixing. Phase contrast and fluorescence images were obtained using filters for DAPI (blue), rhodamine (red), and FITC (green). The DAPI filter set did not eliminate bleed-through of the FITC fluorescence, therefore the FITC labeled cells appear greenish-blue in the micrographs. The target cells labeled with CMAC appear as larger, flat blue cells while the donor cells appear as small, round cells and are labeled both red and green. Relevant target cells are highlighted by a thin white outline in panels A, B, and D. (A) Fusion mediated by wild type G protein at pH 5.9. The phase contrast image shows one small donor cell adjacent to two target cells. Transfer of both DiI and calcein-AM from the donor cell to the target cell (blue) can be seen (arrows). (B) A second plate identical to the one shown in panel A, but maintained at pH 7.0 shows a lack of transfer of DiI or calcein-AM to the outlined target cell, consistent with the requirement for low pH in initiating VSV G-mediated membrane fusion. (C) Fusion mediated by GSHA at pH 7.0. Several donor cells in contact with target cells are shown. Only the transfer of DiI from the donor to the target cells was seen (arrows). There was no transfer of calcein-AM showing that complete fusion had not occurred. (D) Multiple donor cells infected with ? G-VSV which are in contact with an outlined blue target cell is shown, but no transfer of either the DiI or calcein-AM occurred.

FIG. 7 demonstrates that Chlorpromazine (CPZ) can rescue GSHA virus infectivity. Equivalent amounts of GSHA-GFP virus, ΔG-GFP virus and VSV-GFP virus were resuspended in binding media buffered to pH 7.0 and incubated at room temperature for 30 minutes. Following the incubation, the virus suspension was cooled on ice for 10 minutes and then added to BHK-21 cells on ice. Following three hours of binding on ice, the inoculum was removed and the cells were washed with fresh media to remove the unbound virus. Cells were then treated with media containing 0.4 mM CPZ for 1 minute. The drug containing media was removed immediately and the cells were incubated in drug free medium overnight. Twelve hours later the number of cells expressing GFP were counted. The open boxes show the number of GFP positive cells in the absence of CPZ while the hatched boxes indicate the number of GFP positive cells after CPZ treatment. VSV-GFP infected more than 90% of the cells in the presence or absence of CPZ and the GFP cell count is not shown.

Figure 8:
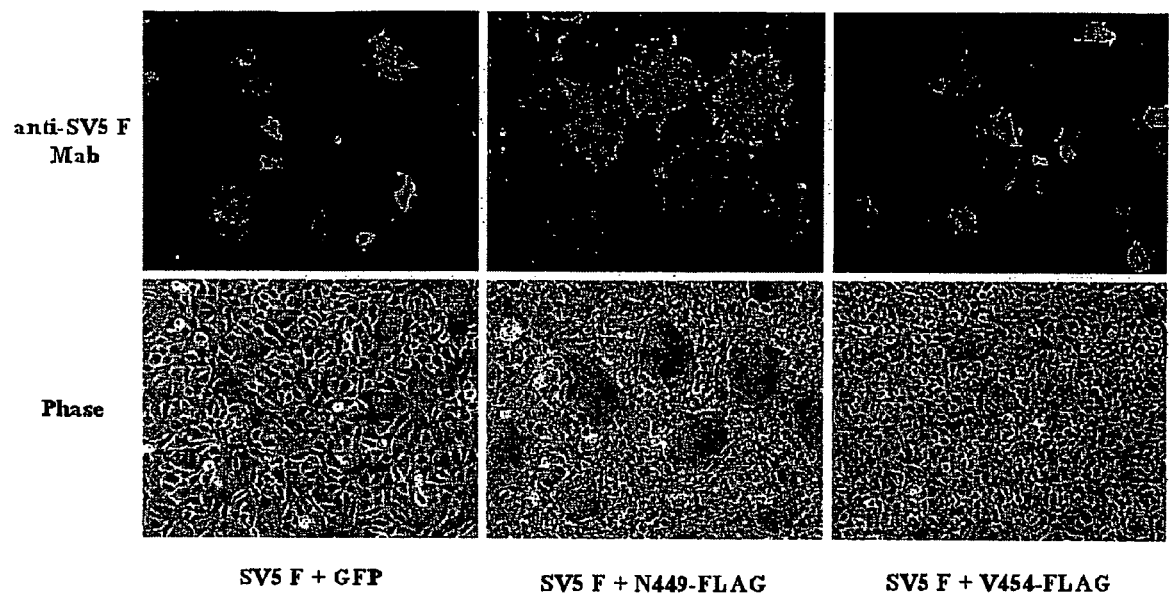

FIG. 8 demonstrates fusion potentiation by GS deletion mutants. BHK-21 cells were co-transfected with plasmids encoding SV5 F and either GFP or the GS truncation mutants which were tagged with the FLAG epitope. At 36 hours post-transfection the cells were fixed and probed with the Fla mAb to detect SV5 F protein. Rhodamine-labeled goat anti-mouse antibody was used to visualize the cells. Phase contrast and epifluorescence images were obtained using a 10× water immersion lens with a Zeiss Axiophot microscope (Germany). At least ten images were obtained for each sample. Representative photomicrographs of cells expressing GS with either 14 amino acids (N449) or 9 amino acids (V454) is shown.

Figure 9:
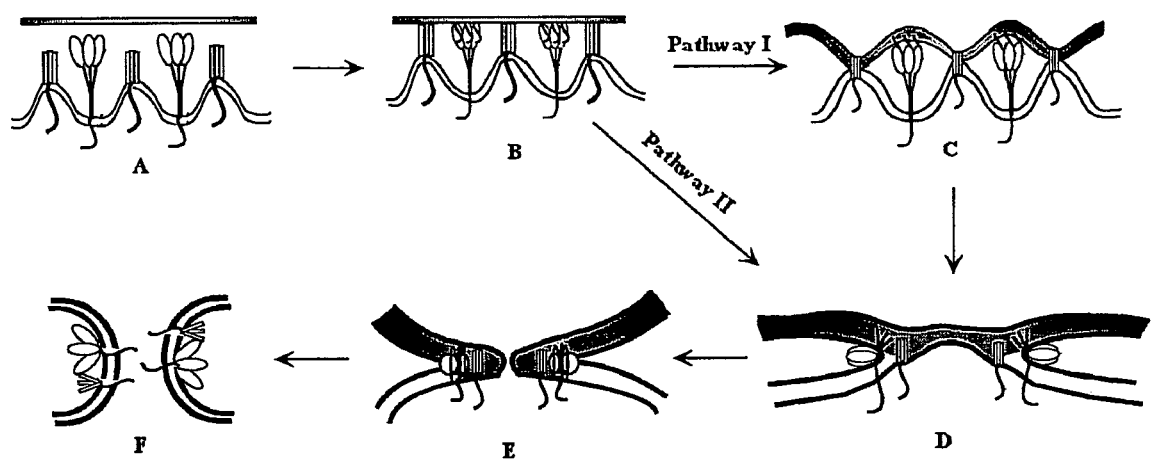

FIG. 9 demonstrates a model for the fusion potentiation of heterologous viral glycoproteins by GS. The membrane at the top of each step represents the target membrane, while the membrane at the bottom, which contains the fusion protein (depicted as a trimeric molecule with globular heads) and GS (depicted as trimeric rectangles), represents the donor membrane. Panels A-E illustrate the pathway towards complete fusion between the two membranes mediated by the viral fusion protein and GS. (A) Two individual membranes before the initiation of fusion. The microdomains where GS is located are shown as having increased membrane curvature. (B) GS alone, or GS and the fusion protein bind to the target membrane which results in close membrane apposition and the initiation of conformational changes in the fusion protein. In pathway I, the fusion protein undergoes additional conformational changes that result in exposure of the fusion peptide which immediately inserts into the target membrane, as shown in panel C. (D) The glycoprotein undergoes further conformational changes that result in formation of the "hairpin" loop intermediate, which is the driving force for membrane merger. Destabilization of the target membrane by the interaction of GS as well as changes induced by the fusion protein causes the formation of a hemifusion diaphragm. In pathway II, the binding events are sufficient to cause GS-mediated hemifusion diaphragm formation (D), which then triggers activation of the fusion protein, release of the fusion peptide, and formation of a hemifusion diaphragm. The unequal forces exerted on the membranes by the lateral movement of protein molecules results in the formation of a fusion pore (E) which then enlarges and completes the fusion reaction (F).

DETAILED DESCRIPTION OF THE INVENTION

The present invention relates to a recombinant Rhabdovirus and methods of generating same. The recombinant Rhabdovirus is engineered to express a Rhabdoviral G stem polypeptide, or a fragment thereof and optionally a heterologous fusion facilitating polypeptide, in strains deleted for the Rhabdoviral glycoprotein (G).

As used herein, the term "recombinant Rhabdovirus" refers to a virus genetically engineered to express proteins not natively expressed in Rhabdoviridae. Engineering of the virus in this manner therefore creates a "pseudotype" or "chimeric" virus that can subsequently be isolated.

In one embodiment, the recombinant Rhabdovirus utilized for this invention is derived from Vesicular Stomatitis Virus (VSV), though the invention provides for the utilization of any virus of the Vesiculovirus and Lysavirus genus. The Vesiculovirus genus includes: Vesicular Stomatitis Virus (VSV) of the New Jersey serotype (VSVNJ), the Indiana serotype (VSVInd), the VSV-Alagoas strain, Cocal virus, Jurona virus, Carajas virus, Maraba virus, Piry virus, Calchaquivirus, Yug Bogdanovac virus, Isfahan virus, Chandipura virus, Perinet virus, and Porton-Svirus (Rose and Whitt. IN B. N. FIELDS' VIROLOGY 4th ED. VOL. 1 (1996)). The Lyssavirus genus includes: Rabies virus (RV), Lagos bat virus, Mokola virus, Duvenhagevirus, Obodhiang virus, and Kotonkan virus (ID.)

Methods for generating recombinant Rhabdoviruses may entail utilizing cDNAs and a Minivirus or a Helper Cell Line. In this case, both "miniviruses" and "helper cells" (also known as "helper cell lines") provide a source of Rhabdoviral proteins for Rhabdovirus virion assembly, which are not produced from the transfected DNA encoding genes for Rhabdoviral proteins.

The generation of recombinant Rhabdovirus can be accomplished using: (1) cDNA's alone; (2) cDNAs transfected into a helper cell in combinations; or (3) cDNA transfection into a cell, which is further infected with a minivirus providing in trans the remaining components or activities needed to produce either an infectious or non-infectious recombinant Rhabdovirus. Using any of these methods (e.g., minivirus, helper cell line, or cDNA transfection only), the minimum components required are an to RNA molecule containing the cis-acting signals for (1) encapsidation of the genomic (or antigenomic) RNA by the Rhabdovirus N protein, and (2) replication of a genomic or antigenomic (replicative intermediate) RNA equivalent.

The term "minivirus" is meant to include incomplete viral particles containing a polycistronic nucleic acid molecule encoding N-P-M-L, N-P-L, N-P-G-L, M-G, G only, M only or any combination of four or fewer Rhabdoviral genes. This incomplete virus particle is incapable of viral replication, a process of the Rhabdoviral lifecycle involving a complete copying of its genome.

Copying of the Rhabdoviral genome, referred to as "Rhabdoviral replication" requires, the presence of a replicating element or replicon, which, herein signifies a strand of RNA minimally containing at the 5' and 3' ends the leader sequence and the trailer sequence of a Rhabdovirus. In the genomic sense, the leader is at the 3' end and the trailer is at the 5' end. Any RNA placed between these two replication signals will in turn be replicated. The leader and trailer regions further must contain the minimal cis-acting elements for purposes of encapsidation by the N protein and for polymerase binding, which are necessary for initiating Rhabdoviral transcription and replication.

In order to produce the recombinant Rhabdovirus of the present invention the cDNA's encoding the modified Rhabdoviral genome listed above must be contacted with a cell under conditions facilitating expression of the vectors employed, permitting production of the recombinant Rhabdovirus. It is to be understood that any cell permitting assembly of the recombinant Rhabdovirus for any one of the three methods disclosed above are included as part of the present invention.

Culturing of Cells to Produce Virus: Transfected cells are usually incubated for at least 24 hours at the desired temperature, usually about 37° C. For generation of infectious virus particles, the supernatant, which contains recombinant virus is harvested and transferred to fresh cells. The fresh cells expressing the G protein (either via transient or stable transfection) are incubated for approximately 48 hours, and the supernatant is collected.

Purification of the Recombinant Rhabdovirus: The terms "isolation" or "isolating" a Rhabdovirus signifies the process of culturing and purifying virus particles such that very little cellular debris remains. One example would be to collect the is virion-containing supernatant and filter (0.2µ pore size) (e.g., Millex-GS, Millipore) the supernatant thus removing Vaccinia virus and cellular debris. Alternatively, virions can be purified using a gradient, such as a sucrose gradient. Recombinant Rhabdovirus particles can then be pelleted and resuspended in whatever excipient or carrier is desired. Viral titers can be determined by serial dilution of supernatant used to infect cells, whereupon following expression o viral proteins, infected cells are quantified via indirect immunofluorescence using for example, anti-M (23H12) or anti-N (10G4) protein specific antibodies (L. Lefrancois et al., (1982) Virology 121: 157-67). It is therefore to be understood that in recombinant Rhabdoviral particles are considered as part of the invention, as well.

For purposes of infecting cells (such as, for example, tissue culture cells or cells from a tissue sample, such as a biopsy), the isolated recombinant Rhabdovirus is incubated with the cells using techniques known in the art. Detection of infection by the recombinant Rhabdovirus could proceed by determining the presence of a reporter gene, such as a green fluorescent protein (GFP), or via assessment of viral protein expression, as determined by indirect immunofluorescence, as discussed above.

To prepare infectious virus particles, an appropriate cell line (e.g., BHK cells) is first infected with vaccinia virus vTF7-3 (T. R. Fuerst et al., (1986) Proc. Natl. Acad. Sci. USA 3. 8122-26) or equivalent which encodes a T7 RNA polymerase or other suitable bacteriophage polymerase such as the T3 or SP6 polymerases (see Usdin et al., (1993) BioTechniques 14:222-224 or Rodriguez et al. (1990) J. Virol. 64:4851-4857). Alternatively, a vaccinia-free system may be utilized which provides an RNA polymerase. The cells are then transfected with individual cDNA containing the genes encoding the N, P, G and L Rhabdoviral proteins. These cDNAs will provide the proteins for building the recombinant Rhabdovirus particle. Cells can be transfected by to any method known in the art (e.g., liposomes, electroporation, etc.).

Thus recombinant Rhabdoviruses and/or particles can be prepared, assembled and isolated. The present invention discloses a recombinant Rhabdovirus comprising a deletion in a nucleic acid sequence encoding a Rhabdoviral G protein, an insertion of a nucleic acid sequence encoding a Rhabdoviral G stem polypeptide or a fragment thereof.

The full nucleic acid sequence encoding for a Rhabdoviral G stem polypeptide is as set forth in SEQ ID No: 1, and is a sequence encoding for a Rhabdoviral G stem polypeptide of the Indiana strain. The full amino acid sequence of a Rhabdoviral G stem polypeptide of the Indiana strain is as set forth in SEQ ID No: 2. Truncations resulting in Rhabdoviral G stem polypeptide fragments are listed in SEQ ID Nos: 3-9, and their functional efficacy is disclosed in the examples section below.

The recombinant Rhabdoviruses of the present invention further comprise a nucleic acid sequence encoding a heterologous fusion facilitating polypeptide. In another embodiment of the present invention, the nucleic acid sequence encoding for a fusion facilitating polypeptide is expressed from a separate transcriptional unit.

The present invention also provides for nucleic acid vectors comprising the recombinant Rhabdoviruses described above. The present invention additionally provides for nucleic acid vectors containing isolated nucleic acids described herein.

The isolated nucleic acid sequences of the present invention comprise Rhabdoviral genomes containing a deletion in the nucleic acid sequence encoding/a Rhabdoviral G protein, and insertion of nucleic acid sequences encoding Rhabdoviral G stem polypeptides or fragments thereof, with or without the inclusion of sequences encoding a heterologous fusion facilitating polypeptide.

In another embodiment, the isolated nucleic acid described may be with or without the inclusion of sequences encoding an anti-receptor for cell targeting.

Another aspect of the present invention provides for an isolated nucleic acid sequence encoding for a Rhabdoviral G stem polypeptide alone. The isolated nucleic acid may contain additional sequences encoding non-Rhabdoviral proteins, such as fusion-facilitating polypeptides and/or anti-receptors for targeting. It is to be understood that these isolated nucleic acid sequences may comprise part of a nucleic acid vector.

In another embodiment, there is provided a recombinant virus comprising a nucleic acid sequence encoding for a Rhabdoviral G stem polypeptide alone. The recombinant virus may comprise additional nucleic acid sequences encoding for a fusion-facilitating peptide and/or an anti-receptor, facilitating direction of the recombinant virus to a target cell. It is to be understood that any virus that may be engineered to include the sequences listed herein are to be considered as part of the invention.

In one embodiment, nucleic acid sequences encoding Rhabdoviral G stem polypeptides, or fragments thereof, correspond to, or are at least 70%, at least 75%, at least 80%, at least 85%, at least 90%, at least 95% or more, including 95%-100%, homologous to the sequence delineated in SEQ ID No: 1. The nucleic acid sequences delineated herein encode for a G stem polypeptide, or a fragment thereof, corresponding to, or being at least 70%, at least 75%, at least 80%, at least 85%, at least 90%, at least 95% or more, including 95%-100%, homologous to SEQ ID No: 2, 4, 5, 6, 7, 8 or 9.

According to another embodiment, nucleic acid vectors comprising the isolated nucleic acid sequences delineated herein include a promoter for regulating expression of the isolated nucleic acid. Such promoters are known to be cis-acting sequence elements required for transcription as they serve to bind DNA dependent RNA polymerase, which transcribes sequences present downstream thereof.

A vector according to the present invention preferably further includes an appropriate selectable marker. The vector may further include an origin of replication, and may be a shuttle vector, which can propagate both in bacteria, such as, for example, *E. coli* (wherein the vector comprises an appropriate selectable marker and origin of replication) and be compatible for propagation in vertebrate cells, or integration in the genome of an organism of choice. The vector according to this aspect of the present invention can be, for example, a plasmid, a bacmid, a phagemid, a cosmid, a phage, a virus or an artificial chromosome.

Consequently, according to yet another aspect of the present invention there is provided a host cell containing the recombinant Rhabdoviruses and/or nucleic acid vectors as described herein. The cell may be a prokaryotic or a eukaryotic cell.

As used herein, the term "Rhabdoviral G protein" is meant to include the glycoprotein (G) encoded by Rhabdoviridae, whose presence contributes to the overall efficiency of the viral budding process (Whitt M. A., (1998) The Journal of Microbiology 36: 1-8). The phrase "G stem polypeptide" or "fragment of a G stem polypeptide" refers to segments of a Rhabdoviral G protein, or polypeptides with at least at least 70%, at least 75%, at least 80%, at least 85%, at least 90%, at least 95% or more, including 95%-100% homology to at least some, and in one embodiment, at least 10 of the 42 membrane-proximal amino acid residues of the G protein ectodomain. In another embodiment, the G stem polypeptide or fragment thereof also includes the transmembrane anchor and cytoplasmic tail regions of the mature G protein.

As is evidenced in the Examples section herein, the G stem protein or polypeptide fragment thereof functions to potentiate membrane fusion. Consequently, utilization of G stem polypeptides may enhance recombinant virus production, viral titers and infectivity via their potentiation of membrane fusion. The addition of a G stem polypeptide can increase infectivity of a Rhabdovirus vector by 10 to 100 fold.

In one embodiment, the G stem polypeptide utilized is comprised of a Rhabdoviral G protein lacking amino acids 1 to 403 of the mature G protein. The G stem polypeptide may comprise between 10 and 42 amino acid residues of the membrane-proximal region of the G protein. The Rhabdoviral G stem polypeptide may be engineered to include an N-terminal epitope tag, of which c-myc, FLAGS®, human influenza hemagglutinin (HA) or polyhistidine (including His6 or His 10) tags may be utilized.

One example of a VSV G stem polypeptide is that derived from the VSV G stem polypeptide of the VSV-Indiana serotype (VSVInd) (GenBank Accession No. 61834). G stem polypeptides derived from VSVInd, beginning with amino acid residue 336 (N) are contemplated herein. More preferred G stem polypeptides are derived from VSVInd G stem polypeptides beginning with residue 392 (T). Most preferred G stem polypeptides include residues spanning 404 (G)-511 (K). Another preferred VSVInd G stem includes the polypeptide comprising 427 (Q)-511 (K), or 440 (F)-511 (K). Other contemplated VSVInd G stems include G stems beginning with residue 404 (G) of the G protein. Less preferred are those VSVInd G stems derived from residues downstream of 449 (N), because although G stems comprising these residues possess a high assembly phenotype, they demonstrate poor potentiation of membrane fusion, as compared to G stem polypeptides derived from residues upstream of 449 (N). The preferred VSVInd G stem polypeptides comprise the entire cytoplasmic tail domain and all of the transmembrane domain of the G protein, as well as portions of the carboxy terminus of the membrane proximal ectodomain (e.g., at least 14 to roughly 127 amino acids of the carboxy terminus of the G protein ectodomain).

Additional G stem polypeptides comprising preferred embodiments of the present invention include the incorporation of similar regions of G proteins derived from all VSV serotypes and all strains within those serotypes, as well as analogous G stem polypeptides derived from alternate Rhabdoviral G proteins. It is to be understood that other polypeptides exhibiting at least 70%, at least 75%, at least 80%, at least 85%, at least 90%, at least 95% or more, including 95%-100%, homology or identity to SEQ ID Nos: 2, 4, 5, 6, 7, 8 or 9 are to be included as part of this invention, as they display sequence homology/identity with Rhabdoviral G stem polypeptides. The invention is also meant to include polypeptides with a lesser degree of homology, yet exhibiting a functional equivalence, in terms of potentiation of membrane fusion are to be considered included as part of this invention.

The recombinant Rhabdovirus of the present invention may be comprised of a nucleic acid sequence encoding for a G stem polypeptide or fragment thereof that is at least 70%, at least 75%, at least 80%, at least 85%, at least 90%, at least 95% or more, including 95%-100% homology or identity to SEQ ID NO: 1, as determined by, for example, the Smith-Waterman algorithm, utilized in analyzing sequence alignment protocols, as in for example, the GAP, BESTFIT, FASTA and TFASTA programs in the Wiconsin Genetics Software Package release 7.0, Genetcis Computer Group, 575 Science Dr., Madison, Wis.).

Alternatively or additionally, polynucleotide homology may be determined by hybridization to SEQ ID NO: 1, which may be effected by stringent or moderate hybridization conditions. An example of stringent hybridization is the use of a hybridization solution containing 10% dextran sulfate, 1 M NaCl, 1% SDS and $5 \times 10^6$ cpm $^{32}$P labeled probe, at 65° C., with a final wash solution of 0.2×SSC and 0.1% SDS and final wash at 65° C.; whereas an example of moderate hybridization would be the use of a hybridization solution containing 10% dextran sulfate, 1 M NaCl, 1% SDS and $5 \times 10^6$ cpm $^{32}$P labeled probe, at 65° C., with a final wash solution of 1×SSC and 0.1% SDS and final wash at 50° C.

The recombinant Rhabdovirus of the invention preferably additionally comprises a fusion facilitating polypeptide participating in G stem mediated potentiation of membrane fusion. As used herein, the term "fusion-facilitating polypeptide" refers to any protein (or fusion-facilitating polypeptide fragment thereof) that following expression on the surface of a vesicular membrane precipitates fusion of the vesicular membrane with a lipid-bilayer encasing a target vesicle or cell. In another embodiment of the present invention, the fusion-facilitating polypeptide is: (1) is derived from a virus characterized as having a lipid envelope; and (2) when expressed as a heterologous protein in a genetically engineered virus, facilitates the fusion of the viral envelope with a cell membrane, resulting in a complete bilayer fusion between participating membranes. It is thus envisioned that a fusion-facilitating polypeptide according to the present invention can function in a non-specific fashion in facilitating the association of an attachment protein on the viral envelope other than the native viral attachment protein. One example of a fusion-facilitating polypeptide as contemplated herein is the viral envelope fusion protein known in the literature as the "F protein" of the SV5 strain of Paramyxoviruses, which specifically is referred to herein as the "F protein" rather than the more generic "F Protein" or "Fusion Protein".

In addition to simian virus 5 (SV5)-derived F proteins, fusion facilitating polypeptides may be selected from HIV envelope proteins, as well as VSV $G_{NJ}$ (New Jersy serotype) or VSV $G_{IND}$ (Indiana serotype) proteins. Also included are polypeptides exhibiting at least 70% amino acid sequence homology to the above mentioned fusion polypeptides, as well as polypeptides exhibiting significant functional homology in terms of stimulating target cell fusion with the recombinant Rhabdoviruses and expressed nucleic acid sequences of the present invention. It is to be understood that utilization of any protein stimulating membrane fusion, or a fragment thereof is to considered within the scope of the invention, as are homologues of such proteins and their fragments, and that these proteins may be of prokaryotic or eukaryotic origin. Proteins and polypeptides derived by protein evolution techniques well known to those skilled in the art are included as well.

The recombinant Rhabdoviruses of the invention, as described above enable potentiation of viral fusion, in the absence of the Rhabdoviral G protein, as a function of expression of fusion facilitating polypeptides, where the additional presence of the Rhabdoviral G stem polypeptide provides for an enhanced rate/magnitude of fusion.

Similarly, prokaryotic and/or eukaryotic cells expressing fusion facilitating polypeptides and Rhabdoviral G stem polypeptides on their cell surfaces may provide a fusion potentiation effect, as a result of surface expression of said polypeptides.

In another embodiment of the invention, there is provided a recombinant virus, comprising a nucleic acid sequence encoding a Rhabdoviral G stem polypeptide or a fragment thereof. The Rhabdoviral G stem polypeptide or fragment thereof, as above, will be at least 70%, at least 75%, at least 80%, at least 85%, at least 90%, at least 95% or more, including 95%-100%, homologous to SEQ ID No:1. The Rhabdoviral G stem polypeptide will comprise between at least 10 and 42 amino acid residues of a membrane-proximal region of the G protein, corresponding to, or at least 70%, at least 75%, at least 80%, at least 85%, at least 90%, at least 95% or more, including 95%-100%, homologous to SEQ ID Nos: 2, 4, 5, 6, 7, 8 or 9. The Rhabdoviral G stem polypeptide or fragment thereof may also comprise a transmembrane anchor and cytoplasmic tail region of a Rhabdoviral G protein, and may additionally contain an N-terminal epitope tag, as described hereinabove.

In another embodiment, the recombinant virus further comprises a nucleic acid sequence encoding a fusion facilitating polypeptide. Other embodiments provide for the inclusion of nucleic acid sequences encoding anti-receptor proteins, or polypeptide fragments thereof, and the inclusion of additional non-Rhabdoviral sequences. The invention provides for a vector, a cell, a liposome or a viral particle comprising the recombinant virus herein disclosed, as well as compositions comprising some or all of these elements, as will be discussed further hereinbelow.

The present invention provides for a method of potentiating target cell fusion, comprising the steps of contacting the cell with an effective amount of a recombinant Rhabdoviral particle as described herein, where the recombinant Rhabdoviral particle envelope fuses with a membrane of a target cell at a rate or quantity greater than fusion of wild-type Rhabdoviral particles alone, thereby potentiating target cell fusion.

In another embodiment of the present invention, the method of potentiating target cell fusion, comprising contacting the target cell with an effective amount of cells expressing the recombinant Rhabdoviruses or isolated nucleic acid molecules/vectors described herein, where the membrane of the cell expressing the recombinant Rhabdoviruses or isolated nucleic acid molecules/vectors fuses with a membrane of a is target cell at a rate or quantity greater than fusion of wild-type cells alone, thereby potentiating target cell fusion.

It is to be understood that any vector, or cell expressing such a vector, encoding Rhabdoviral G stem polypeptides or fragments thereof, alone, or in combination with heterologous fusion facilitating polypeptides, are to be considered part of the present invention.

In keeping with this, in another embodiment of the invention, target cell fusion is potentiated via contacting a cell with an effective amount of recombinant virus, recombinant viral particles, or cells expressing the recombinant virus, as disclosed herein.

As a result of the disclosure herein of a fusion-potentiation effect mediated by a G stem polypeptide or fragment thereof, encoded by a negative-stranded RNA virus, including Rhabdoviridae, the present invention additionally relates to a method of interfering with, inhibiting or abrogating cell fusion. The method comprises the steps of contacting target cells infected with a Rhabdovirus, with an effective amount of an inhibitor of a Rhabdoviral G stem polypeptide or a fragment thereof, wherein the administration of the inhibitor serves to prevent expression or function of the Rhabdoviral G stem polypeptide, thereby interfering with, inhibiting or abrogating cell fusion.

In one embodiment, the target cells are infected with a negative stranded RNA virus, and the inhibitor is directed against a nucleic acid or a polypeptide that is at least 70% homologous to nucleic acid sequences encoding, or polypeptide sequences comprising Rhabdoviral G stem polypeptides, as disclosed herein. Rhabdoviral G stem polypeptide inhibitors may comprise isolated nucleic acid or recombinant viruses comprising an antisense molecule, siRNA or ribozyme directed against a nucleic acid molecule encoding for the Rhabdoviral G stem polypeptide. Construction of these inhibitors are by methods well known to one skilled in the art (See for example US Patent Application No. 20020086356A1 or Welch et al., Clin Diagn Virol. (1998) 10: 163-71).

In another embodiment, the Rhabdoviral G stem polypeptide inhibitor comprises a chemical inhibitor or the polypeptide preventing protein function. The inhibitor may comprise an antibody or antibody fragment, the design of which is via methodology well known to those skilled in the art.

The present invention further provides a means of directing recombinant Rhabdoviruses, and cells expressing translated products of the recombinant sequences delineated herein, to a particular cell. Direction may be a function of cell type per se, or differentiation state, or other factors, such as specific direction to infected cells within a given tissue.

The term "specific cell targeting" or "targeted cell" is therefore meant to refer to modifications introduced into the recombinant Rhabdoviruses, recombinant viruses, or cells expressing the translated products of the recombinant sequences delineated herein, facilitating direction of the virus/cell to interact with a particular cell. For example, as will be described, it will be possible to direct recombinant Rhabdoviruses to tumor cells expressing the surface marker erbB. Such erbB$^+$ cells, in turn, would be referred to herein as "target cells" as these cells are the population with which the recombinant virus/cell expressing nucleic acids comprising sequences corresponding to the recombinant Rhabdovirus will ultimately fuse. Target cells often express a surface marker (referred to herein as "target antigen") that may be utilized for directing the recombinant Rhabdovirus to the cell, as opposed to neighboring cells, that are not tumor to cells in origin and hence do not express erbB. Similarly, appropriately manipulated prokaryotic or eukaryotic cells engineered to incorporate nucleic acid sequences corresponding to those found in recombinant Rhabdoviruses, may be utilized, with these cells expressing targeting moieties, as above, on their cell surfaces.

The target antigen may be a receptor, therefore an "antireceptor," also referred to as "attachment protein," signifies a protein displayed on a recombinant Rhabdoviral envelope, or cell surface as described above, responsible for attachment of the viral particle/modified cell to its corresponding "receptor" on the target cell membrane. For example, the native antireceptor of the parармyxovirus SV5 is the viral HN protein, which binds sialic acid on host cell membranes. Fusion thus accomplished is mediated via the binding of an attachment protein (or "antireceptor") on the viral envelope to a cognate receptor on the cell membrane.

As used herein, the term "attachment" refers to the act of antireceptor (expressed on viral particle lipid envelopes or engineered cell sufaces) recognition and binding to a target cell surface "receptor" during infection. The skilled artisan will recognize that attachment occurs prior to fusion of the attaching membrane with the target cell plasma membrane.

The anti-receptor proteins or polypeptide fragments thereof may be derived from members of the following viral families: Arenaviridae, Bunyaviridae, Coronaviridae, Filoviridae, Flaviviridae, Herpesviridae, Hepadnaviridae, Orthomyxoviridae, Paramyxoviridae, Poxyiridae, Retroviridae, and Rhabdoviridae. Additional viral targeting agents may be derived from the following: African Swine Fever Virus, Borna Disease Virus, Hepatitis X, HIV-1, Human T Lymphocyte virus type-I (HTLV-1), HTLV-2, 1 5 lentiviruses, Epstein-Barr Virus, papilloma viruses, herpes simplex viruses, hepatitis B and hepatitis C.

Bacterial proteins expressed during intracellular infection are also potential targets contemplated for therapeutic intervention by recombinant Rhabdovirus of the present invention. The intracellular bacteria may include, amongst others: *Shigella, Salmonella, Legionella, Streptococci, Mycobacteria, Francisella* and *Chlamydiae* (See G. L. Mandell, "Introduction to Bacterial Disease" IN CECIL TEXTBOOK OF MEDICINE, (W.B. Saunders Co., 1996) 1556-7). These bacteria would be expected to express a bacteria-related protein on the surface of the infected cell to which the recombinant Rhabdovirus would attach.

Proteins of parasitic agents, which reside intracellularly, also are targets contemplated for infection by the recombinant Rhabdovirus. The intracellular parasites contemplated include for example, Protozoa. Protozoa, which infect cells, include: parasites of the genus *Plasmodium* (e.g., *Plasmodium falciparum, P. Vivax, P. ovale* and *P. malariae*), *Trypanosoma, Toxoplasma, Leishmania*, and *Cryptosporidium*.

Diseased and/or abnormal cells may be targeted using the recombinant Rhabdoviruses and modified cells by the methods described above. The diseased or abnormal cells contemplated include: infected cells, neoplastic cells, pre-neoplastic cells, inflammatory foci, benign tumors or polyps, cafe au lait spots, leukoplakia, and other skin moles.

The recombinant Rhabdoviruses will be targeted using an anti-receptor that will recognize and bind to its cognate receptor or ligand expressed on the diseased or abnormal cell. Fusion of the recombinant Rhabdoviral virion is dependant upon incorporation of a fusion facilitating protein as previously described.

Similarly, cells may be engineered to express Rhabdoviral genome components, by methods well known in the art. Nucleic acid vectors comprising the Rhabdoviral G stem polypeptide may be expressed in conjunction with a fusion facilitating polypeptide, on the expressing cell surface. Additional incorporation of "anti-receptor" proteins, or polypeptide fragments thereof, facilitates specific targeting of the expressing cell to the target cell, and provides for fusion of the two cell types. Possible anti-receptors used in the recombinant Rhabdovirus will include the natural anti-receptor for any particular cell receptor.

Alternatively, recombinant Rhabdoviruses and modified cells can be further engineered to express an antibody or polypeptide fragment thereof, a bi-functional antibody, Fab, Fc, Fv, or single chain Fv (scFv) as their attachment protein. Such antibody fragments may be constructed to identify and bind to a specific receptor. These antibodies can be humanized, human, or chimeric antibodies (for discussion and additional references see S. L. Morrison "Antibody Molecules, Genetic Engineering of," in MOLECULAR BIOLOGY AND BIOTECHNOLOGY: A COMPREHENSIVE DESK REFERENCE 1995; S. D. Gillies et al., (1990) Hum. Antibod. Hybridomas 1(1): 47-54; E. HARLOW AND D. LANE, ANTIBODIES: A LABORATORY MANUAL (1988) Cold Spring Harbor Press, NY). Expression of functional single chain antibodies on the surface of viruses has been reported using Vaccinia virus (M. C. Galmiche et al., (I 997) J. Gen. Virol. 78: 3019-3027). Similar methods would be utilized in creating a recombinant Rhabdovirus expressing a fusion facilitating protein and an antibody or antibody fragment. The genes encoding monoclonal antibodies that target, for example, tumor associated antigens (TAAs) expressed on a cell surface (e.g., prostate specific antigen (PSA)), can be isolated and used to produce the desired recombinant Rhabdovirus, or subcloned into an appropriate expression vector and expressed on a cell surface, as described above, through methodology well known to an individual skilled in the art.

For example, the genes encoding antibodies recognizing TAAs can be fused to the Rhabdoviral G stem for anchoring the antibody protein or polypeptide fragment thereof within the viral membrane. Examples of antibodies include those antibodies, which react with malignant prostatic epithelium but not with benign prostate tissue (e.g., ATCC No. HB-9119; ATCC HB-9120; and ATCC No. HB-1 1430) or react with malignant breast cancer cells but not with normal breast tissue (e.g., ATCC No. HB-8691; ATCC No. HB-10807; and 21HB-108011). Other antibodies or fragments thereof, which react with diseased tissue and not with normal tissue, would be apparent to the skilled artisan.

For purposes of targeting cells in vivo, the isolated recombinant Rhabdovirus or cells expressing Rhabdoviral G stem polypeptides and additional components described above, could be administered by intravascular (i.v.), intramuscular (i.m.), intranasal (i.n.), subcutaneous (s.c.), oral, rectal, intravaginal, or by any means in which the recombinant virus can be delivered to tissue (e.g., needle or catheter). Alternatively, topical administration may be desired for insertion into epithelial cells. Another method of administration is via aspiration or aerosol formulation.

The routes of administration utilized for recombinant Rhabdoviruses facilitate viral circulation, attachment and infection, thereby enabling viral expression of encoded proteins, which may be assayed via the incorporation of reporter proteins within the recombinant Rhabdovirus. It is expected that following Rhabdoviral administration viral protein expression, (as determined, for example, by reporter protein detection) should occur within 24 hours and certainly within 36 hours.

As disclosed herein, the present invention further provides a method for targeted cell or tissue lysis, the method comprising contacting a cell or tissue with an effective amount of a recombinant Rhabdovirus. The recombinant Rhabdovirus comprises a genome containing a deletion in the nucleic acid sequence encoding a G protein, an insertion of a nucleic acid sequence encoding a Rhabdoviral G stem polypeptide, a nucleic acid sequence encoding a heterologous fusion facilitating polypeptide and a nucleic acid sequence encoding an anti-receptor protein or a polypeptide fragment thereof, wherein the anti-receptor protein or a polypeptide fragment thereof binds to a cognate receptor or ligand that is associated with the target cell and that is expressed on the surface of the target cell or tissue, facilitating Rhabdoviral entry and thereby specific lysis of the target cells or tissue. When the term "effective amount" is utilized in this context, it therefore refers to the amount of Rhabdovirus necessary to produce lysis in targeted cells or tissue. The terms "cognate receptor" and "ligand" refer to surface exposed moieties imparting specificity to their interaction with molecules expressed on the target cell or vesicle.

In another embodiment of this aspect of the invention, the targeted cell or tissue is diseased, and the anti-receptor binds a cell surface marker whose expression is a function of the diseased state of the cell or tissue. Targeted lysis of diseased cells or tissue is therefore therapeutic, resulting in destruction of diseased cells alone, and not neighboring, healthy cells that differ in terms of cell surface expression of the target antigen, thereby facilitating control of the disease. For example, recombinant Rhabdoviral targeting may result in specific destruction of tumor cells, without damaging neighboring healthy cells, selectively inhibiting tumor growth, and facilitating disease control. Additionally, targeted lysis of diseased cells may impart further activation to a developing local immune response via a "by-stander" effect, or, via direct activation, such as, for example, via stimulation of expression of immune system costimulatory molecules. Hence the vectors, cells and compositions comprising the recombinant Rhabdovirus and isolated nucleic acids may function as a vaccine for a specific disease or condition. It is to be understood that the recombinant Rhabdovirus and isolated nucleic acids alone may be similarly utilized as vaccines for preventative or prophylactic application.

Some diseases contemplated for use with the targeted recombinant Rhabdovirus and nucleic acid therapeutic lysis protocols discussed above are cancer, cell proliferative disorders, inflammatory cell disorders and infection.

Other aspects of the present invention include the provision of compositions comprising a Rhabdoviral vector for administration to a cell or to a multi cellular organism. The Rhabdoviral vectors of the invention may be employed in combination with a non-sterile or sterile carrier or carriers for administration to cells, tissues or organisms, such as a pharmaceutical carrier suitable for administration to an individual. Such compositions comprise, for instance, a media additive or a therapeutically effective amount of a recombinant virus of the invention and a pharmaceutically acceptable carrier or excipient. Such carriers may include, but are not limited to, saline, buffered saline, dextrose, water, glycerol, and combinations thereof. The formulation should suit the mode of administration.

The invention further relates to diagnostic and pharmaceutical packs and kits comprising one or more containers filled with one or more of the ingredients of the aforementioned compositions of the invention.

The recombinant vectors of the invention may be employed alone or in conjunction with other compounds, such as therapeutic compounds.

The pharmaceutical compositions may be administered in any effective, convenient manner including, for instance, administration by intravenous, intraperitoneal, intramuscular, subcutaneous, intranasal or intradermal routes among others. In therapy or as a prophylactic, the active agent may be administered to an individual as an injectable composition, for example as a sterile aqueous dispersion, preferably isotonic. The pharmaceutical compositions of the invention are preferably administered by injection to achieve a systematic effect against relevant viral pathogens.

For administration to mammals, and particularly humans, it is expected that the physician will determine the actual dosage and duration of treatment, which will be most suitable for an individual and can vary with the age, weight and response of the particular individual.

The following examples are presented in order to more fully illustrate the preferred embodiments of the invention. They should, in no way be construed, however, as limiting the broad scope of the invention.

EXAMPLES

Materials and Methods

Plasmids and Oligonucleotide-Directed Mutagenesis

The construct pCAGGS-GS$^{HA}$ was obtained by subcloning an MluI and NheI fragment encoding GS$^{HA}$ from pVSV-ΔG-GS$^{HA}$ (41) into a modified form of the eukaryotic expression vector pCAGGS (32). The constructs pCAGGS-G$_{124}$-E, A$_{133}$-K, P$_{127}$-D, D$_{137}$-L and Qn-1 were obtained by subcloning MluI and NheI fragments from the appropriate GMMG mini-genomes (13).

The constructs pCAGGS-CD4-G and CD4-GS (CD4 ectodomain fused to GS at F421) were prepared by subcloning the KpnI to SphI restriction digest fragments encoding CD4-G and CD4-GS from VSV-ΔG-CD4-G/GS (41) into the pCAGGS vector previously digested with the same enzymes. To produce ΔG-F the cDNA encoding the fusion protein (F) from the paramyxovirus simian virus 5 (SV5) (36) was subcloned into pVSV-ΔG-PL from pGEM-F (kindly provided by R. A. Lamb, Northwestern University) using the XhoI site, and clones were screened for proper orientation. The SV5-F cDNA was then moved from ΔG-F into pCAGGS by using the KpnI-NheI sites to produce pC-SV5-F. Plasmids containing the measles virus F and H proteins (pCG-F and pCG-H5, respectively) and the corresponding antibodies were generously provided by Dr. Roberto Cattaneo, Mayo Clinic (5b). The cDNA for the Moloney murine leukemia virus envelope protein was provided by Dr. Lorraine Albritton (University of Tennessee Health Science Center).

Epitope Tagged Truncation Mutants of GS

Consecutive seven amino acid (aa) truncations of GS, beginning with an amino acid containing an N-terminal FLAG or HA epitope tag (FIG. 1) were generated, as follows. The HA epitope tags were generated by PCR using a sense-strand oligonucleotide that overlapped the 3' end of the M-gene (MT-954) and an antisense oligonucleotide (5'AGGATGA CCCGAGCCAGCGTAATCTGGTACATCATACGG-3') (SEQ ID NO: 10) that overlapped the HA epitope (in italics) in the template ΔG-GS$^{HA}$ (41) and that contained the unique AvaI site (underlined), for cloning purposes. The FLAG epitope tagged mutants were generated via PCR using the MT-954 sense primer and an antisense primer (5'GA CCCGAGCCCTTATCGTCATCATCTTTGTAGTCGAAC TTGCAATTCACCCCA ATG-3') (SEQ ID NO: 11) that overlapped the signal sequence of G protein (indicated in bold type) and that contained the unique AvaI site (underlined). The PCR fragments were digested with the enzymes MluI and AvaI. The GS fragments corresponding to residues Q$_{427}$, P$_{434}$, F$_{440}$, S$_{447}$ and V$_{454}$ were obtained by restriction digestion of the corresponding pBluescript CD4-GS constructs (41) with AvaI and SphI. The epitope tag and the fragments encoding the appropriate GS were cloned into the plasmid pVSV-ΔG-PL (+) (41) that had been previously digested with MluI and SphI in a 3-way ligation reaction. The mutants N449, L453 and E452 were constructed by PCR-based mutagenesis using individual sense-strand oligonucleotides that had a common 5' sequence (5'-ATGGCCTCGGGT . . . ) (SEQ ID NO: 13) which contained an AvaI site (underlined) followed by the sequence coding for the amino acid residue N449, L453 and E452, respectively and an antisense oligonucleotide, (5'CCAAACATGAAGCTTCTGTTGT GCATGCTTTGAGTTAC-3') (SEQ ID NO: 12), which introduced an SphI site (underlined) within the 3' untranslated region of the G in pVSVFL-2 (+) (23). The amplicons were digested with AvaI and SphI and cloned into pVSV-ΔG-PL (+) together with the FLAG or HA epitope encoding fragments via 3-way ligation reaction. The sequences of the PCR amplified fragments were confirmed by dideoxynucleotide sequencing. The constructs were then subcloned into pCAGGS-MCS as MluI and SphI fragments.

The construct gp160$_{w3I}$GS was made by a PCR-based mutagenesis approach. This glycoprotein is composed of the gp120-gp41 ectodomain from HIV-1 clone BH10 (39) through residue 671 which is connected by a linker encoding Ile-Ser-Gly to the C-terminal portion of VSV-G$_{IND}$ at residue 454. The gp160$_{w3I}$GS cDNA was constructed by amplifying the sequence encoding the transmembrane-ectodomain junction of HIV-1 gp160 from plasmid pBH10 using a sense-strand oligonucleotide (5'-TGGATGGAGTGGGACAG-3') (SEQ ID NO: 14) (BH10-CR1+), and the non-coding primer (5'-GTTAT ACCCGAGATATTCCACAAACTTGCCCATTTATC-3') (SEQ ID NO: 15) (BH10-W3IAva), which introduced an AvaI site (underlined), and substituted the codon for tryptophan at position 672 of gp160 with an isoleucine codon (bold faced) (44) The amplicon was digested with HindIII and AvaI and then ligated together with an EcoRI-HindIII fragment from wt-BH10 into the EcoRI-AvaI digested vector pGEM-CD4-V$_{454}$ (41). The resulting construct was subcloned as an EcoRI-SphI fragment into pCAGGS-MCS, resulting in pC-gp160$_{w3I}$GS (a.k.a. pC-W3IGS). This chimera expresses the HIV Env protein at high levels on the cell surface and retains the same chemokine receptor tropism as WT BH10 Env.

Transient Transfections and Syncytium Assays

Approximately 7×10$^5$ baby hamster kidney (BHK-21) cells were transfected with a DNA: liposome suspension containing 2 μg of the appropriate plasmid and 10 μl of lipofectamine (GIBCO-BRL) according to the manufacturer's instructions. Three hours post-transfection, the media was replaced with Dulbecco's modified Eagles medium (DMEM) containing 10% fetal bovine serum (FBS) and the cells were incubated for 36 hours at 37° C. Cells were then fixed with 3% paraformaldehyde and processed for indirect immunofluorescence microscopy. Syncytia formation with HIV-env expressing cells was done as follows. Approximately 7×10$^5$ BHK-21 cells were transfected with pCAGGS plasmids encoding GS$^{HA}$, CD4, CD4-G or CD4-GS alone or co-transfected with plasmids expressing CD4-G and GS$^{HA}$. After 24 hours, the cells were removed from the dish using trypsin-EDTA and then replated either alone or mixed with cells expressing gp160$_{w3I}$GS. The cultures were incubated at 37° C. for an additional 24 hours and then cells were fixed with 3% paraformaldehyde and probed with a monoclonal antibody (Sim.2) specific for the CD4 molecule or with a monoclonal antibody specific for the HA epitope.

Antibodies

The following antibodies were used for staining the cells in the syncytia assays. The F1a monoclonal antibody (mAb), which is specific for the SV5 F protein, was a kind gift of Dr. R. A. Lamb, Northwestern University and Dr. Rick Randall, St. Andrews University (38). The Sim.2 mAb (28, 34), which binds to the CD4 ectodomain and the goat-anti-gp160 sera HT3 (27) was obtained through the NIH AIDS Research and Reference Reagent Program, Division of AIDS, National Institute of Allergy and Infectious Diseases, National Institute, of Health. The other antibodies that were used include mAb VIII, which is specific for the VSV G$_{NJ}$ glycoprotein (4), mAbs 12CA5 MAb and HA.11 (Covance, USA) which are specific for the HA epitope, and M2 (Sigma-Aldrich, Switzerland) which is specific for the FLAG epitope.

Recovery of G-Stem Viruses from cDNA

Virus recovery was conducted as previously described (49) with the following modifications. Confluent monolayers of BHK-21 cells in 35 mm plates were infected with a recombinant Vaccinia virus encoding the T7 RNA polymerase (vTF7-3) (15) at a multiplicity of infection (MOI) of 5 for 1 hour at 31° C. The cells were then transfected with a DNA: liposome suspension consisting of 5 μg of pVSV-ΔG-GS$^{HA/FLAG}$, 3 μg, 5 μg, 8 μg and 1 μg, respectively of plasmids containing the N, P, G and L genes from VSV$_{IND}$ and 90 μl of TransfectACE (43, 52). After 3 hours, the transfection mix was replaced with DMEM containing 10% FBS and cells were incubated at 37° C. The supernatants were collected after 48 hours and filtered through a 0.2μ filter (Millipore, Millex-GS) to remove vaccinia virus. The filtrates were then applied to BHK-21 cells, which had been transfected with 2 μg of pCAGGS-G$_{IND}$ 24 hours earlier. Recovery of the virus was assessed by examining the cells for cytopathic effects that are typical of a VSV infection after 24-36 hours. The recovered viruses were plaque purified and then passaged on BHK-21 cells expressing G protein to make high titer G-complemented virus stocks. Expression of the G-stem proteins in virus infected cells was confirmed by immunofluorescence microscopy using antibodies specific for the HA or FLAG epitopes.

Preparation of Non-G Complemented GS Viruses

To produce GS virus stocks that have no full-length G protein in their envelopes (non-G complemented viruses) BHK-21 cells were infected with the G-complemented stock viruses at an MOI of 10. One hour post-infection the inoculum was removed and the cells were washed twice with serum free DMEM (SF-DMEM) and once with medium containing G-protein specific monoclonal antibody (I1) (24) to remove any residual G-complemented virus inoculum that may be present in the supernatants. At 16 hours post-infection, the supernatants were collected and the virus particles were pelleted through a 20% sucrose cushion by ultracentrifugation. The viral pellet was resuspended in sterile Dulbecco's phosphate buffered saline (dPBS) and stored at −80° C. until further use.

Viral Binding Assay

Viral binding was conducted as previously described (12). Approximately, 80,000 cpm of [$^{35}$S]-methionine labeled WT-VSV, non-G complemented GS$^{HA}$ or ΔG virus was added to 500 μl of binding media (2 mM Na$_2$HPO$_4$, 2 mM NaH$_2$PO$_4$, 30 mM NaCl, 2 mM 2-[N-morpholino]-ethanesulfonic acid (IVIES), and 2 mM N-2-hydroxyethylpiperazine-N'-2-ethanesulfonic acid (HEPES), 0.1% BSA, DMEM, titrated to pH 7.0 or pH 5.9 with HCl) and incubated at room temperature for 30 minutes. Virus suspensions were cooled on ice for 10 minutes and then added to confluent monolayers of BHK-21 cells that had been pre-washed with ice-cold binding media at the appropriate pH. Virus adsorption was done for 3 hours on ice. The is inoculum was removed and the amount of unbound virus in the supernatants was determined via scintillation counting. Cells were washed 3 times with ice-cold binding media and the amount of virus eluted in the wash was determined as above. Cells were then solubilized with PBS containing 1% triton X-100 (TX-100) and the amount of bound virus was determined.

Cell-Cell Fusion Assays

The assay was based on the redistribution of fluorescent probes between donor cells and target cells upon fusion. The fluorescent probes DiI-DS, calcein-AM and CMAC were obtained from Molecular Probes (Eugene, Oreg.). The assay was conducted as described previously (30) with the following modifications.

a) Preparation of donor cells: BHK-21 cells ($7 \times 10^6$) were infected with WT-VSV, $GS^{HA}$ or $\Delta G$ virus at an MOI=10. At 2 hours post-infection, the cells were washed twice with SF-DMEM and once with I1 MAb to remove any unbound G-complemented virus. At 8 hours post-infection, the cells were incubated with 10 µM calcein-AM in D-PBS for 30 minutes at 37° C., washed twice with SF-DMEM to remove excess dye and then incubated in fresh DMEM+5% FBS. After 2 hours, the cells were labeled with DiI by incubating the cells in D-PBS containing 5 µM of DiI-DS for 20 minutes at 37° C., according to the manufacturer's instructions. Cells were washed three times with SF-DMEM to remove the unincorporated label. Labeled cells were then removed from the plates using PBS containing 50 mM EDTA, washed two times with D-PBS (changing tubes each time) and resuspended in 1 ml of SF-DMEM.

b) Preparation of target cells: Three hours prior to the assay, $4 \times 10^6$ BHK-21 cells in 6 cm dishes were labeled with the blue fluorescent dye CMAC by incubating them for 30 minutes at 37° C. with D-PBS containing 20 µM of CMAC. Cells were washed two times with SF-DMEM and then incubated with fresh DMEM+5% FBS at 37° C. for 3 hours.

The donor cells were overlayed on the CMAC-labeled target cells and the culture was incubated at 4° C. for one hour to allow the donor cells to settle and make contact with the target cells. Unbound cells were then removed by washing twice with pre-warmed SF-DMEM and the attached cells were incubated at 37° C. for 15 minutes in 2 ml of SF-DMEM. Fusion was triggered by incubating cells for 1 minute at room temperature with fusion medium (10 mm $Na_2HPO_4$, 10 mM $NaH_2PO_4$, 150 mM NaCl, 10 mM 2-[N-morpholino]ethanesulfonic acid (IVIES), 10 mM N-2-hydroxyethylpiperazine-N'-2-ethanesulfonic acid (HEPES)) buffered to pH 7.0 or pH 5.9. The fusion medium was immediately replaced with SF-DMEM and fusion was allowed to proceed for 30 minutes at 37° C. The cells were then incubated on ice to arrest fusion. Phase-contrast and fluorescence micrographs were acquired using a 40× water immersion lens on a Zeiss Axiophot microscope equipped with a Zeiss Axiocam digital camera and accompanying AxioVision software. Images were adjusted for brightness and contrast using Adobe Photoshop 6.0 after conversion to tiff files.

Chlorpromazine (CPZ) Rescue Assay

Stocks of VSV-GFP virus (19), non-G complemented $GS^{HA}$-GFP (41) and non-G complemented $\Delta G$-GFP virus (41) were produced in BHK cells. Virions were concentrated by ultra-centrifugation, and an aliquot of the viral pellet was loaded on a 10% SDS-PAGE gel and stained with Coomassie blue (GelCode Blue, Pierce Chemical Company). Virus quantitation was based on L-protein concentration using ImageQuant software (Molecular Dynamics).

The assay was conducted as previously described (54) with the following modifications. An equivalent amount of each virus, based on viral protein content, was added to 500 µl of binding buffer (pH 7.0) and the virus suspension was incubated at room temperature for 30 minutes. The virus suspension was cooled on ice for 10 minutes and then added to pre-chilled BHK-21 cells on ice. Virus adsorption was conducted on ice for 3 hours. The inoculum was removed, cells were rinsed with pre-warmed DMEM containing 10% FBS and incubated at 37° C. for 10 minutes. Cells were then treated with DMEM+10% FBS containing CPZ (0.4 mM) for 1 minutes, washed twice, returned to drug-free medium immediately and incubated at 37° C. for 2 hours to allow the cells to recover from the effect of the drug. Cells were then overlayered with DMEM containing 5% FBS and 0.5% methylcellulose. Twelve hours later the cells were examined using a fluorescence microscope (Zeiss Axiophot, Germany) and the number of GFP positive cells were counted.

Example 1

Potentiation of the Fusion Activity of Heterologous Viral Glycoproteins by GS $GS^{HA}$ (G-stem or GS containing a N-terminal hemagglutinin [HA] epitope tag) is a truncation mutant of the Rhabdoviral G protein in which amino acids 1 to 404 of the mature protein have been deleted. FIG. 1A shows the amino acid sequence of the membrane proximal ectodomain of GS. The Applicants have previously demonstrated that $GS^{HA}$ is a trimer, that it is transported to the cell surface and that it is important for efficient assembly and budding of VSV particles (41).

Figure 2:
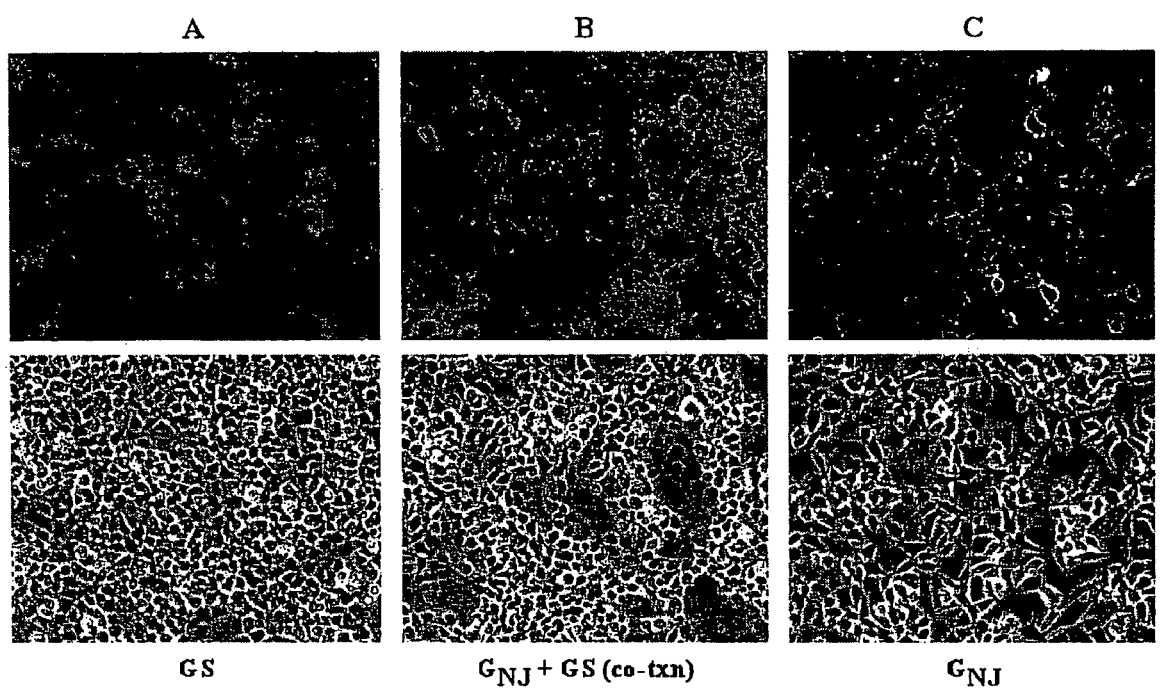

While conducting studies on GS-mediated viral assembly, the Applicants noticed that cells co-expressing GS and another membrane fusion protein produced extensive and large syncytia, but when GS was expressed alone no syncytia were observed. This phenomenon is illustrated in FIG. 2. Panel A shows an example of cells expressing $GS^{AH}$ only and the absence of syncytia. For comparison when $GS^{HA}$ was co-expressed with the VSV $G_{NJ}$ (New Jersey serotype) glycoprotein, and the culture maintained at neutral pH, large, well-defined areas of cell-cell fusion could be seen (Panel B). The same results were obtained when $GS^{HA}$ was co-expressed with the VSV $G_{IND}$ (Indiana serotype) protein (data not shown). Normally, when cells expressing VSV G are maintained at neutral pH very little to no syncytia formation occurs, as is seen when $G_{NJ}$ was expressed alone (Panel C). These results suggested that GS could relieve the normal low pH activation step required for VSV G mediated membrane fusion and could functionally potentiate the fusion activity of the Rhabdoviral G protein.

Although it is well-established that VSV G protein requires a low pH trigger to obtain the fusion competent conformation (11, 3, 35), the Applicants have found that when G protein is overexpressed at very high levels in BHK-21 cells the G proteins of both the Indiana and New Jersey serotypes can induce some cell-cell fusion at neutral pH (42). The ability of VSV G to cause cell-cell fusion without prior exposure to low pH and the possible mechanism by which this occurs in the polarized endometrial cell line HEC-1A has been described previously (40). Therefore, it is more likely that the GS-mediated fusion potentiation observed following co-expression of GS with $G_{NJ}$ or $G_{IND}$ is not due to activation of G protein, per se, but rather to an enhancement of the low level fusion activity normally present in cells expressing VSV G protein.

Figure 3:
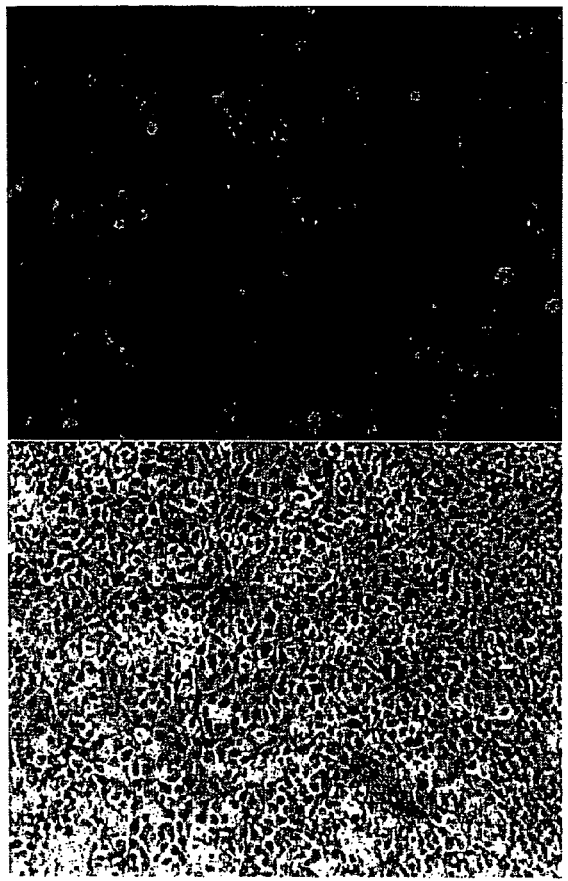
Figure 3:
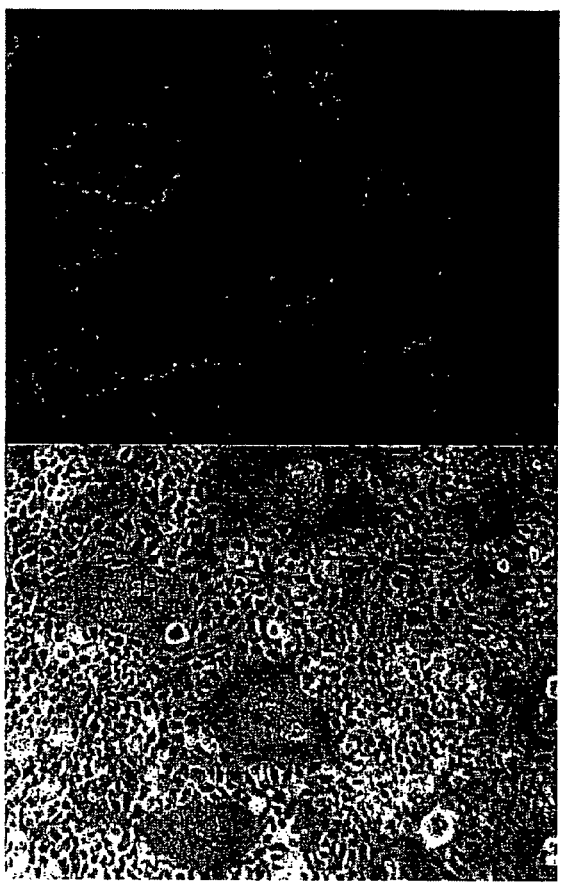

To determine if GS could potentiate the membrane fusion activity of other viral glycoproteins, the Applicants coexpressed GS$^{AH}$ with the simian virus 5 (SV5) F protein. SV5 (strain W3A) F protein can directly induce membrane fusion in the absence of its cognate HN protein (18). When SV5 F protein was expressed alone in cells a few small syncytia containing 4-5 nuclei were observed (FIG. 3A). However, when GS$^{AH}$ was co-expressed with SV5 F protein there was a dramatic increase in the number of syncytia formed and in the size of the syncytia (FIG. 3B). By 36 hours after transfection giant polykaryons having 100-150 nuclei per syncytium were observed.

Figure 4:
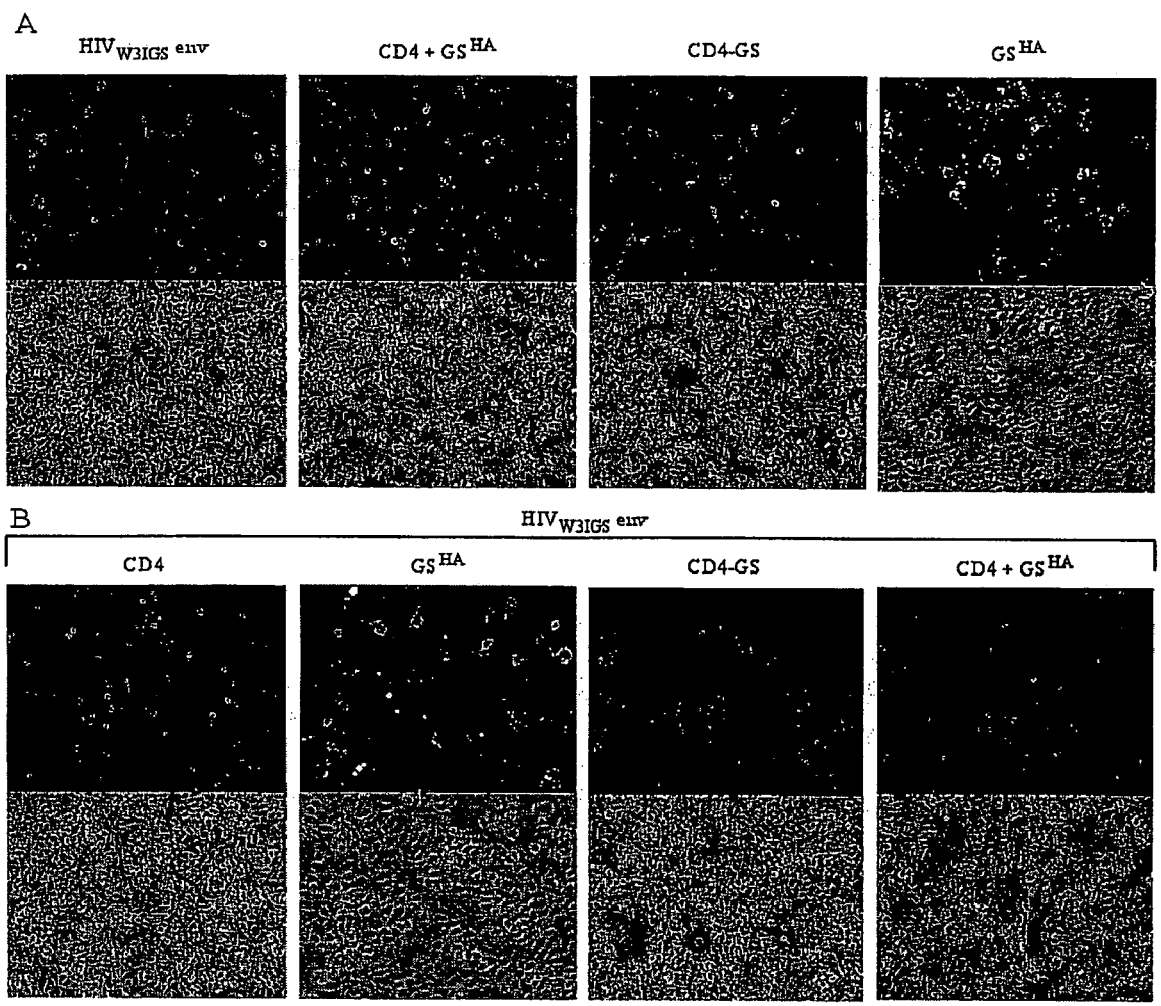

To determine the extent to which GS could enhance the membrane fusion activity of other viral glycoproteins, the Applicants next asked if GS had an effect on HIV-1 env mediated fusion. For these studies the Applicants used a cell fusion assay in which non-human (BHK-21) cells expressing an X4-specific HIV envelope protein derived from the clone BH10 were mixed with cells expressing either human CD4 alone, CD4 and GS, or a CD4-GS chimera previously described (41). As expected, no syncytia were seen in the control cells expressing i) HIV-1 env alone, ii) CD4 and GS$^{HA}$ together, iii) a CD4-GS chimera alone, or iv) GS$^{HA}$ alone (FIG. 4A). Likewise, when BHK-21 cells expressing HIV-1 env were mixed with BHK-21 cells expressing CD4 (FIG. 4B, left-hand most panel) no detectable cell-cell fusion occurred, which is consistent with previous studies demonstrating a requirement for a chemokine co-receptor for HIV-1 Env-mediated membrane fusion (10, 5a). Similarly, when cells expressing HIV-1 env were mixed with cells expressing GS$^{HA}$ only, no cell fusion occurred (FIG. 4B), demonstrating GS$^{HA}$ alone is insufficient to induce cell fusion. However, when cells co-expressed CD4 and GS$^{HA}$, or cells expressing the CD4-GS chimera were mixed with cells expressing the HIV-1 envelope protein a large number of syncytia were seen (FIG. 4B, two right-hand most panels). These results confirmed that GS could function with a variety of different envelope proteins. More remarkable though was the observation that GS could apparently relieve the chemokine coreceptor requirement for CD4-dependent HIV-1 Env-mediated membrane fusion. As will be reported elsewhere, GS can function with a wide variety of different HIV-1 and HIV-2 envelope proteins, therefore GS fusion potentiation is not restricted to enhancement of the gp160$_{W3A}$GS envelope clone.

In contrast to the results described above, when GS was co-expressed with measles virus (MV) F protein, no discernable cell-cell fusion was observed. In contrast to the SV5 F protein, MV F protein required coexpression of viral H protein for membrane fusion activity, as evidenced by enhanced syncytium formation following MV F and H proteins coexpression with GS. A summary of the results that were obtained by coexpressing GS$^{HA}$ with various viral glycoproteins is shown in Table 1.

TABLE 1

| Glycoprotein | Fusion enhancement by GS$^a$ |
|---|---|
| 1) G$_{IND}$ | +/++ |
| 2) G$_{NJ}$ | ++/+++ |
| 3) SV5 F | ++++ |
| 4) MoMuLV | + |
| 5) HIV$_{W3/GS}$ | ++++ |
| 6) Measles F | − |
| 7) Measles F + H | +/− |

The results demonstrate that GS can potentiate the fusion activity of some but not all viral glycoproteins and that the fusion potentiating activity can occur with glycoproteins that require a pH trigger as well as those that are pH independent. This suggests that GS functions at a point common to both fusion pathways.

Example 2

Fusion Potentiation by GS Requires a Fully Functional Viral Glycoprotein

The Applicants next asked if GS could relieve the fusion defects of some G protein mutants that have been described previously. The mutants that were used for these assays were A133-K (14) and QN-1 (53), which have no detectable fusion activity, and D137-L, G124-E and P127-D (14, 13), which have a reduced pH threshold for fusion and can fuse as well as wild type G protein at a pH below 5.7. All the mutants have wild type (wt) G protein cell binding activity. When the Applicants co-expressed these constructs with GS in BHK-21 cells there was no enhancement of membrane fusion, indicating that GS did not rescue the fusion defective phenotypes of these mutants when cells were maintained at neutral pH or at pH 5.9 (data not shown). These results together with the results from the MV F experiment (Table 1) indicated that fusion potentiation by GS requires a fully functional viral glycoprotein.

Example 3

Induction of Cell Binding by GS

Figure 5:
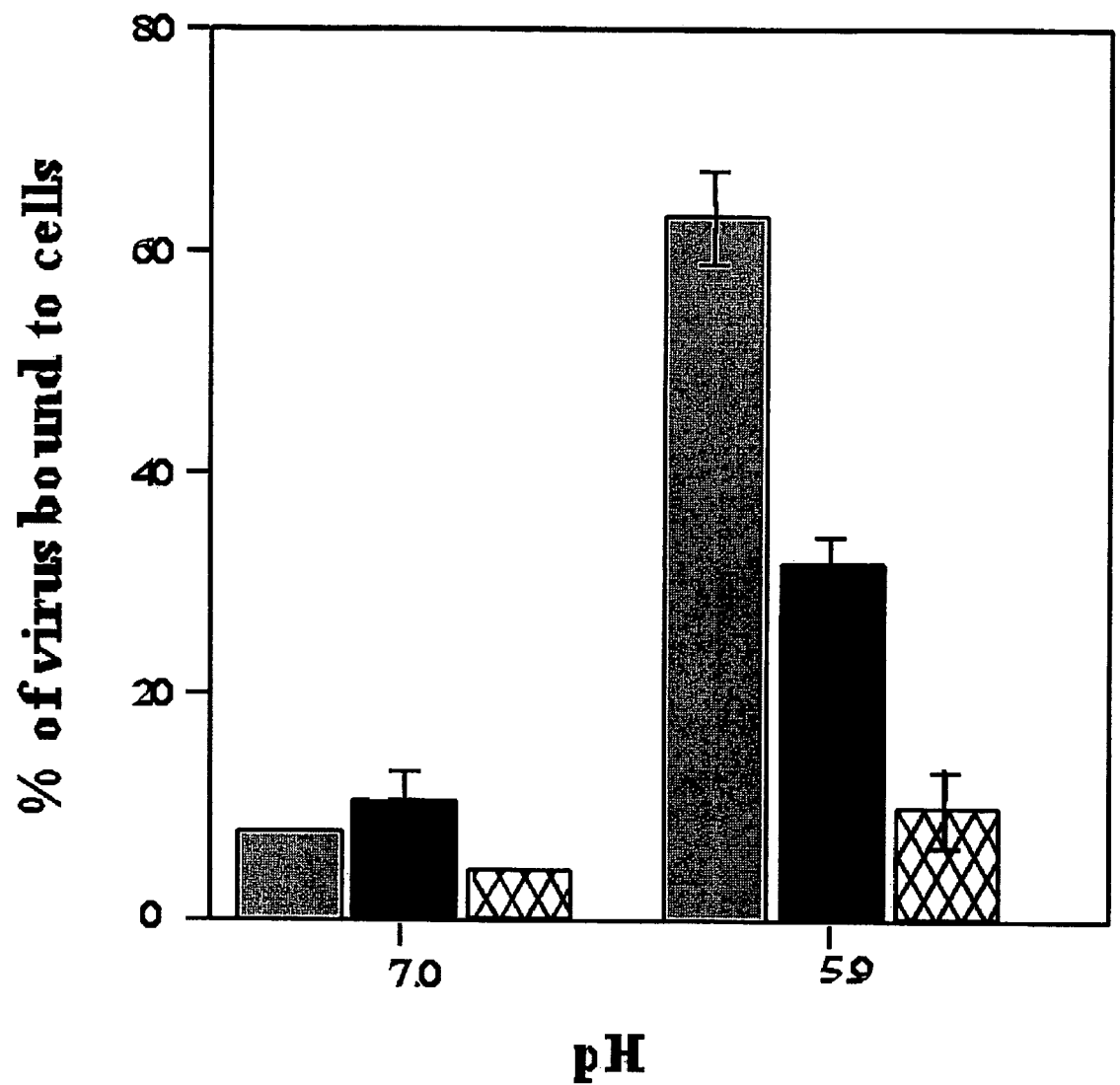

To understand the basis for the membrane fusion enhancing activity of GS, the Applicants performed a series of experiments designed to examine various steps in the fusion process. The first step of glycoprotein-mediated membrane fusion requires binding of the glycoprotein to the target membrane. To determine whether GS exhibits cell-binding activity, radiolabeled GS$^{HA}$ virus was incubated with BHK-21 cells in ice-cold media buffered to pH 7.0 or pH 5.9 for 3 hours. Wild type VSV (WT) served as the positive control while "bald" viruses lacking G protein (ΔG virus) served as the negative control for binding. Virus binding was conducted on ice to prevent endocytosis of the virus as well as to inhibit fusion of the viral envelope with the host cell membranes following exposure to acidic pH. As shown in FIG. 5, GS$^{HA}$ virus can bind to cells similar to WT-VSV at pH 7.0. However, at acidic pH the binding of WT-VSV increased by 5-6 fold while the binding of GS$^{HA}$ increased by only 2-3 fold. Similar results were obtained with a GS virus that lacked the HA epitope (data not shown), demonstrating that the HA epitope tag did not significantly contribute to the binding properties of GS. The small amount of binding of ΔG virus to the cells at both of the pH values examined was considered non-specific background binding. These observations indicate that GS can mediate binding of the virus to target cell membranes. This binding could potentially bring two membranes in close proximity to initiate the fusion reaction.

Example 4

Induction of Hemifusion by GS

Figure 6:
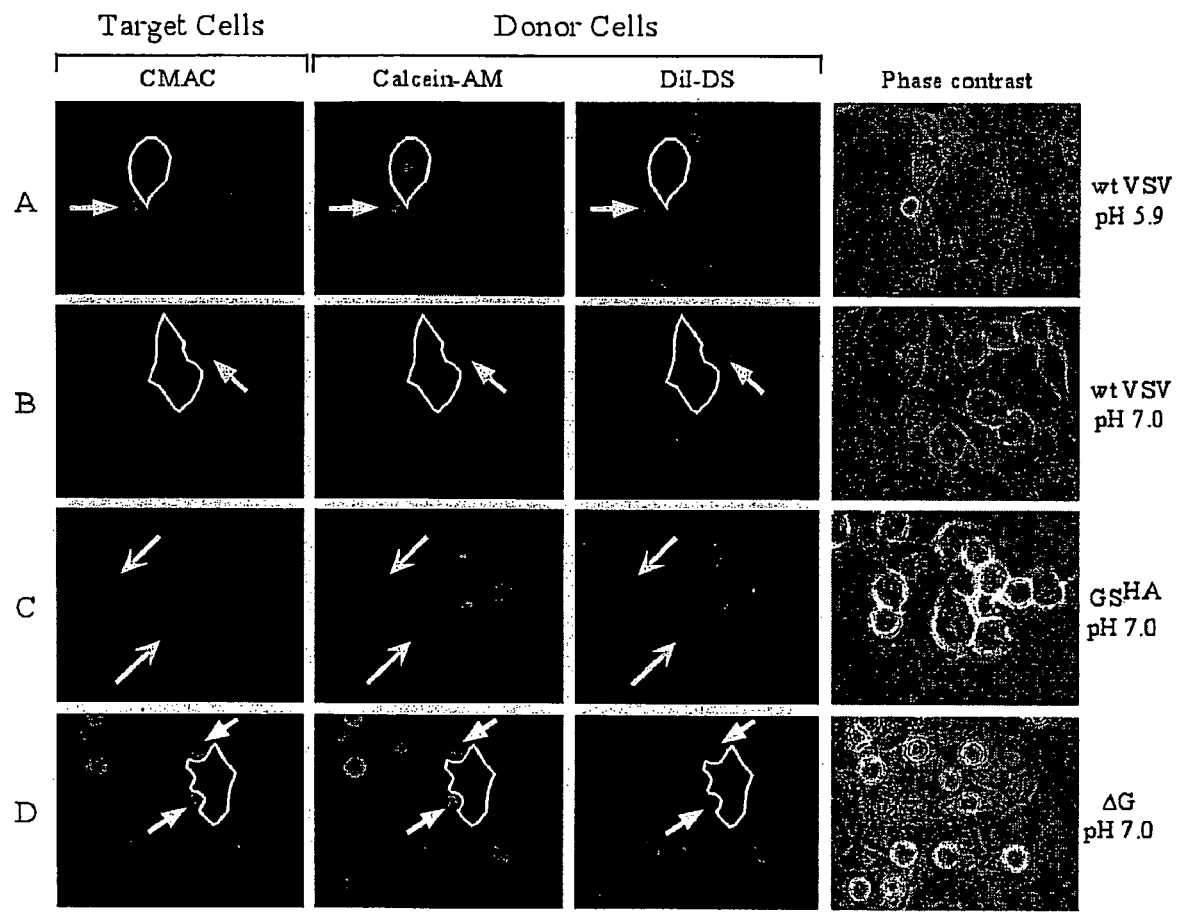

The Applicants next examined whether GS could mediate the next step in the fusion pathway, namely the mixing of the outer leaflets of the two membranes. For this analysis the Applicants used a 3-color fusion assay similar to that described previously for other viral fusion proteins (30). In this assay BHK-21 cells were infected with WT virus, $GS^{HA}$ virus, or ΔG virus, functioning as the donor cells. By six hours post-infection the virus infected cells expressed high levels of either G protein or $GS^{HA}$ on their plasma membranes (data not shown). Virus-infected donor cells were then labeled with a red lipidic dye (DiI-DS) and a green cytoplasmic dye (calcein-AM). The target cells were labeled with a blue cytoplasmic dye (CMAC). The donor cells were then coincubated for 1 hour with the target cells via overlay, on ice, to facilitate cell attachment. After warming the culture to 37° C. for 15 minutes, fusion was triggered by incubating the cells in fusion medium buffered to pH 5.9 or 7.0 for 1 minute. This assay is based on the redistribution of the dyes between the donor cell and target cell during the fusion process. When membrane fusion occurs the donor cells redistribute the lipidic dye DiI first and then upon opening of the fusion pores calcein-AM is transferred to the cytoplasm of the target cell. The dye CMAC forms a glutathione adduct with a molecular wt of ~600 Da within the cytoplasm of the target cells that cannot pass through the small fusion pores and thus helps in distinguishing the target cells from donor cells (31). If there is redistribution of DiI only to the target cells, this indicates that outer leaflet mixing has occurred, but that the fusion reaction did not proceed to completion. Mixing of the outer leaflet only is known as the hemi-fusion stage. If both DiI and calcein-AM are transferred to the target cells then complete fusion has occurred. As shown in FIG. 6A, when cells infected with WT-VSV were mixed with the target cells (blue) and exposed to pH 5.9 cell fusion occurred, as indicated triple staining with DiI, calcein-AM and CMAC (arrows). For comparison, when cells were maintained at a pH of 7.0 (FIG. 6B) there was no transfer of either DiI or calcein-AM to the target cells. These results are consistent with previous studies using an octadecylrhodamine (R18) dequenching assay which demonstrated a VSV G protein requirement for a low pH trigger for fusion initiation, as measured by lipidic dye exchange (2, 37). In contrast to the pH dependent fusion activity of Rhabdoviral G protein, cells expressing $GS^{HA}$ transferred DiI at pH 7.0 (FIG. 6C); however, no transfer of calcein-AM occurred even after exposure to pH 5.9 (data not shown). These data indicate that $GS^{HA}$ can induce hemifusion, but not pore formation. The lipid mixing and content mixing events observed with WT-VSV infected cells or the hemifusion induced by $GS^{HA}$ were not seen in ΔG virus infected cells at either pH 7.0 (Panel D) or at pH 5.9 (data not shown).

Example 5

Rescue of $GS^{HA}$ Virus Infection by Chlorpromazine (CPZ)

Figure 7:
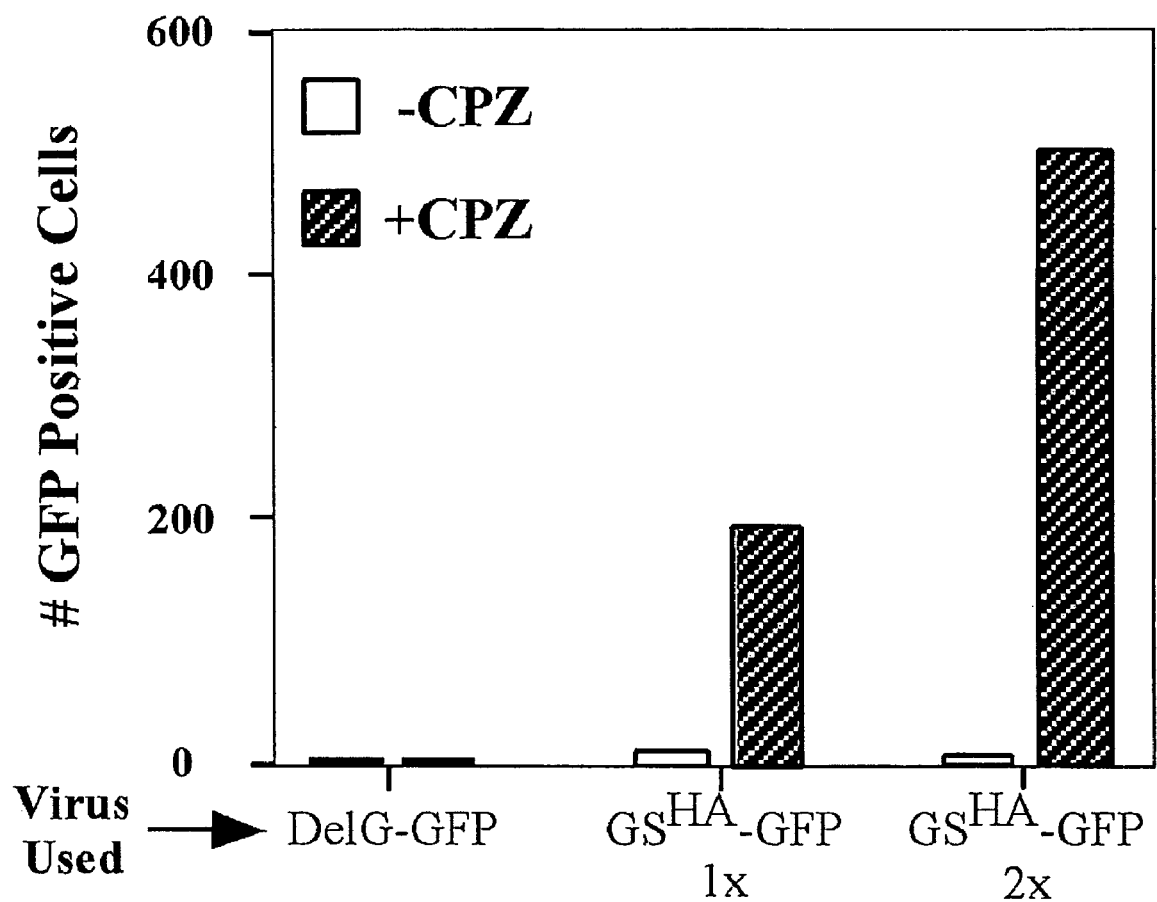

To determine if GS induced lipid mixing, as measured by DiI transfer, was a biologically relevant lipid destabilization event, the Applicants examined whether the membrane curvature agent CPZ could rescue $GS^{HA}$ virus infection. CPZ is an aliphatic phenothiazinea that can destabilize hemifusion diaphragms and drive the formation of a fusion pore (6). CPZ has been used previously to rescue hemifusion intermediates of influenza heamagglutinin (29), and MoMuLV glycoprotein (54). For this assay, $GS^{HA}$-GFP virus bound to cells at 4° C. enabled the formation of GS-dependent hemifusion diaphragms, when cells were shifted to 37° C. The cells were then treated with 0.4 mM CPZ for 1 minute and incubated overnight in drug free media. The number of GFP positive cells in the presence or absence of CPZ was then quantified. GFP expression can occur only if the virus successfully entered the cells and initiated replication. As shown in FIG. 7, when cells prebound with $GS^{HA}$ virus were treated with CPZ (hatched boxes) there was a 200- to 500-fold increase in the number of GFP positive cells as compared to cells that were not treated with CPZ. Increasing the amount of $GS^{HA}$ virus used for the assay resulted in a proportional increase in the number of GFP positive cells. In contrast, CPZ treatment of cells pre-bound with ΔG-GFP virus resulted in no GFP positive cells. As expected WT-VSV-GFP virus was able to infect and spread throughout the culture in the presence or absence of CPZ (data not shown). These data indicate that GS can induce lipid mixing which results in the formation of a biologically functional hemifusion diaphragm. Therefore, the basis for GS-mediated fusion potentiation likely results from the ability of GS to induce the formation of a hemifusion diaphragm thereby reducing the energy barrier for membrane fusion.

Example 6

Deletion Analysis of the GS Fusion Potentiation Domain

To determine how much of the G protein ectodomain is required for GS fusion potentiation, a series of G protein deletion mutants were generated. Constructs were generated containing nucleotide coordinates 1-273 of SEQ ID No: 1 (corresponding to nucleotide coordinates 1289-1562 and amino acid coordinates 421-497 of the VSV G protein), and truncations thereof to generate G stem polypeptides (FIG. 1A). Each of the constructs was N-terminally tagged with either of two epitopes (FLAG or HA) to monitor GS surface expression. All constructs examined expressed GS on the cell surface with no difference detected in expression levels of any of the proteins, regardless of the epitope tag used (data not shown). Constructs containing nucleic acid sequences encoding for 9, 14, 16, 23, 29, 36 and 42 amino acid (aa) residues of the G protein membrane-proximal ectodomain (SEQ ID Nos: 3-9, respectively), additionally including the transmembrane and cytoplasmic domains (amino acid residues 463-511 of SEQ ID No: 2) of the protein were prepared. The Applicants discovered that GS containing 14 amino acid (aa) residues of the membrane-proximal ectodomain (beginning with residue 449 (N) of the mature G protein) (SEQ ID No: 4) or more (residues 449 (N)-462 (K) of the mature G protein) (SEQ ID Nos: 5-9) were able to potentiate the fusion activity of SV5 F while a construct containing 9 aa residues (beginning with residue 454 (N)) (SEQ ID No: 3) resulted in no fusion potentiation (FIG. 8). These results revealed that as few as 14 aa of GS are sufficient for the fusion potentiation function of GS.

REFERENCES

1. Berger, E. A., P. M. Murphy, and J. M. Farber. 1999. Chemokine receptors as HIV-1 coreceptors: roles in viral entry, tropism, and disease. Annu Rev Immunol. 17:657-700.
2. Blumenthal, R., A. Bali-Puri, A. Walter, D. Covell, and O. Eidelman. 1987. pH-dependent fusion of vesicular stomatitis virus with Vero cells. J. Biol. Chem. 262:13614-13619.
3. Blumenthal, R., A. Bali-Puri, A. Walter, D. Covell, and O. Eidelman. 1987. pH-dependent fusion of vesicular stomatitis virus with Vero cells. Measurement by dequenching of octadecyl rhodamine fluorescence. J Biol. Chem. 262: 13614-13619.

4. Bricker, B. J., R. M. Snyder, J. W. Fox, W. A. Volk, and R. R. Wagner. 1987. Monoclonal antibodies to the glycoprotein of vesicular stomatitis virus (New Jersey serotype): A method for preliminary mapping of epitopes. Virology. 161:533-540.

5a. Broder, C. C., D. S. Dimitrov, R. Blumenthal, and E. A. Berger. 1993. The block to HIV-1 envelope glycoprotein-mediated membrane fusion in animal cells expressing human CD4 can be overcome by a human cell component(s). Virology. 193:483-491.

5b. Catomen, T., H. Y. Hussein, and R. Cattaneo. 1998. Measles viruses with altered envelope protein cytoplasmic tails gain cell fusion competence. J. Virol. 72: 1224-1234.

6. Chemomordik, L., A. Chanturiya, J. Green, and J. Zimmerberg. 1995. The hemifusion intermediate and its conversion to complete fusion: regulation by membrane composition. Biophys J. 69:922-929.

7. Doms, R. W., and J. P. Moore. 2000. HIV-1 membrane fusion: targets of opportunity. J. Cell Biol. 151:9-14.

8. Durrer, P., Y. Gaudin, R. W. H. Ruigrok, R. Graf, and J. Brunner. 1995. Photolabeling identifies a putative fusion domain in the envelope glycoprotein of rabies and vesicular stomatitis viruses. J. Biol. Chem. 270:17575-17581.

9. Fan, D. P., and B. M. Sefton. 1978. The entry into host cells of Sindbis virus, vesicular stomatitis virus, and Sendai virus. Cell. 15:985-992.

10. Feng, Y., C. C. Broder, P. E. Kennedy, and E. A. Berger. 1996. HIV-1 entry cofactor: functional cDNA cloning of a seven-transmembrane, G protein-coupled receptor. Science. 272:872-877.

11. Florkiewicz, R. Z., and J. K. Rose. 1984. A cell line expressing vesicular stomatitis virus glycoprotein fuses at low pH. Science. 225:721-723.

12. Fredericksen, B. L., and M. A. Whitt. 1998. Attenuation of recombinant vesicular stomatitis viruses encoding mutant glycoproteins demonstrate a critical role for maintaining a high pH threshold for membrane fusion in viral fitness. Virology. 240:349-358.

13. Fredericksen, B. L., and M. A. Whitt. 1996. Mutations at two conserved acidic amino acids in the glycoprotein of vesicular stomatitis virus affect pH-dependent conformational changes and reduce the pH threshold for membrane fusion. Virology. 217:49-57.

14. Fredericksen, B. L., and M. A. Whitt. 1995. Vesicular stomatitis virus glycoprotein mutations that affect membrane fusion activity and abolish virus infectivity. J. Virol. 69:1435-1443.

15. Fuerst, T. R., P. L. Earl, and B. Moss. 1987. Use of a hybrid vaccinia virus-T7 RNA polymerase system for expression of target genes. Mol Cell Biol. 7:2538-2544.

16. Gaudin, Y., H. Raux, A. Flamand, and R. W. H. Ruigrok. 1996. Identification of amino acids controlling the low-pH-induced conformational change of rabies virus glycoprotein. J. Virol. 70:7371-7378.

17. Helenius, A. 1993 Influenza virus fusion: From models towards a mechanism. p. 89-111. In J. Bentz (ed.), Viral fusion mechanisms, vol. 1. CRC press, Ann Arbor.

18. Horvath, C. M., R. G. Paterson, M. A. Shaughnessy, R. Wood, and R. A. Lamb. 1992. Biological activity of paramyxovirus fusion proteins: factors influencing formation of syncytia. J. Virol. 66:4564-4569.

19. Jayakar, H. R., K. G. Murti, and M. A. Whitt. 2000. Mutations in the PPPY motif of vesicular stomatitis virus matrix protein reduce virus budding by inhibiting a late step in virion release. J Virol. 74:9818-9827.

20. Jeetendra, E. and Whitt, M. A. 2001. Characterization of the minimal budding domain in the vesicular stomatitis virus (VSV) glycoprotein, p. 96: W19-2. 20th Annual Meeting of the American Society for Virology, University of Wisconsin-Madison, Madison, Wis.

21. Kreis, T. E., and H. F. Lodish. 1986. Oligomerization is essential for transport of vesicular stomatitis virus glycoprotein to the cell surface. Cell. 46:929-937.

22. Kuzmin, P. I., J. Zimmerberg, Y. A. Chizmadzhev, and F. S. Cohen. 2001. A quantitative model for membrane fusion based on low-energy intermediates. Proc Natl Acad Sci USA. 98:7235-7240.

23. Lawson, N., E. Stillman, M. A. Whitt, and J. K. Rose. 1995. Recombinant vesicular stomatitis viruses from DNA. Proc. Natl. Acad. Sci. (USA). 92:4477-4481.

24. Lefrancois, L., and D. S. Lyles. 1982. The interaction of antibody with the major surface glycoprotein of vesicular stomatitis virus. I. Analysis of neutralizing epitopes with monoclonal antibodies. Virology. 121:157-167.

25. Li, Y., C. Drone, E. Sat, and H. P. Ghosh. 1993. Mutational analysis of the vesicular stomatitis virus glycoprotein G for membrane fusion domains. J. Virol. 67:4070-4077.

26. Marsh, M., and A. Helenius. 1989. Virus entry into animal cells. Adv. Virus Res. 36:107-151.

27. Matsushita, S., M. Robert-Guroff, J. Rusche, A. Koito, T. Hattori, H. Hoshino, K. Javaherian, K. Takatsuki, and S. Putney. 1988. Characterization of a human immunodeficiency virus neutralizing monoclonal antibody and mapping of the neutralizing epitope. J. Virol. 62:2107-2114.

28. McCallus, D. E., K. E. Ugen, A. I. Sato, W. V. Williams, and D. B. Weiner. 1992. Construction of a recombinant bacterial human CD4 expression system producing a bioactive CD4 molecule. Viral Immunol. 5:163-172.

29. Melikyan, G. B., S. A. Brener, D. C. Ok, and F. S. Cohen. 1997. Inner but not outer membrane leaflets control the transition from glycosylphosphatidylinositol-anchored influenza hemagglutinin-induced hemifusion to full fusion. J Cell Biol. 136:995-1005.

30. Munoz-Barroso, I., S. Durell, K. Sakaguchi, E. Appella, and R. BlumenthaL 1998. Dilation of the human immunodeficiency virus-1 envelope glycoprotein fusion pore revealed by the inhibitory action of a synthetic peptide from gp41. J Cell Biol. 140:315-323.

31. Munoz-Barroso, I., K. Salzwedel, E. Hunter, and R. Blumenthal. 1999. Role of the membrane-proximal domain in the initial stages of human immunodeficiency virus type 1 envelope glycoprotein-mediated membrane fusion. J Virol. 73:6089-6092.

32. Niwa, H., K. Yamamura, and J. Miyazaki. 1991. Efficient selection for high-expression transfectants with a novel eukaryotic vector. Gene. 108:193-199.

33. Ohnishi, S.-I. 1988. Fusion of viral envelopes with cellular membranes. Curr. Topics in Membranes and Transport. 32:257-298.

34. Oravecz, T., and M. A. Norcross. 1993. Costimulatory properties of the human CD4 molecule: enhancement of CD3-induced T cell activation by human immunodeficiency virus type 1 through viral envelope glycoprotein gp120. AIDS Res Hum Retroviruses. 9:945-955.

35. Paternostre, M. T., R. J. Lowy, and R. Blumenthal. 1989. pH-dependent fusion of reconstituted vesicular stomatitis virus envelopes with Vero cells. Measurement by dequenching of fluorescence. FEBS Lett. 243:251-258.

36. Paterson, R. G., S. W. Hiebert, and R. A. Lamb. 1985. Expression at the cell surface of biologically active fusion and hemagglutinin/neuraminidase proteins of the paramyxovirus simian virus 5 from cloned cDNA. Proc Natl Acad Sci USA. 82:7520-7524.

37. Puri, A., M. Krumbiegel, D. Dimitrov, and R. Blumenthal. 1993. A new approach to measure fusion activity of cloned viral envelope proteins: fluorescence dequenching of octadecylrhodamine-labeled plasma membrane vesicles fusing with cells expressing vesicular stomatitis virus glycoprotein. Virology. 195:855-858.
38. Randall, R. E., D. F. Young, K. K. Goswami, and W. C. Russell. 1987. Isolation and characterization of monoclonal antibodies to simian virus 5 and their use in revealing antigenic differences between human, canine and simian isolates. J Gen Virol. 68:2769-2780.
39. Ratner, L., W. Haseltine, R. Patarca, K. J. Livak, B. Starcich, S. F. Josephs, E. R. Doran, J. A. Rafalski, E. A. Whitehorn, K. Baumeister, and et al. 1985. Complete nucleotide sequence of the AIDS virus, HTLV-III. Nature. 313:277-284.
40. Roberts, P. C., T. Kipperman, and R. W. Compans. 1999. Vesicular stomatitis virus G protein acquires pH-independent fusion activity during transport in a polarized endometrial cell line. J Virol. 73:10447-10457.
41. Robison, C. S., and M. A. Whitt. 2000. The membrane-proximal stem region of vesicular stomatitis virus G protein confers efficient virus assembly J Virol. 74:2239-2246.
42. Robison I V, C. S. 2001. Ph.D. University of Tennessee Health Science Center.
43. Rose, J. K., L. Buonocore, and M. A. Whitt. 1991. A new cationic liposome reagent mediating nearly quantitative transfection of animal cells. BioTechniques. 10:520-525.
44. Salzwedel, K., J. T. West, and E. Hunter. 1999. A conserved tryptophan-rich motif in the membrane-proximal region of the human immunodeficiency virus type 1 gp41 ectodomain is important for Env-mediated fusion and virus infectivity. J Virol. 73:2469-2480.
45. Schnell, M. J., J. E. Johnson, L. Buonocore, and J. K. Rose. 1997. Construction of a novel virus that targets HIV-1-infected cells and controls HIV-1 infection. Cell. 90:849-857.
46. Shokralla, S., R. Chemish, and H. P. Ghosh. 1999. Effects of double-site mutations of vesicular stomatitis virus glycoprotein G on membrane fusion activity. Virology. 256:119-129.
47. Shokralla, S., Y. He, E. Wanas, and H. P. Ghosh. 1998. Mutations in a carboxy-terminal region of vesicular stomatitis virus glycoprotein G that affect membrane fusion activity. Virology. 242:39-50.
48. Suarez, T., W. R. Gallaher, A. Agirre, F. M. Goni, and J. L. Nieva. 2000. Membrane interface-interacting sequences within the ectodomain of the human immunodeficiency virus type 1 envelope glycoprotein: putative role during viral fusion. J Virol. 74:8038-8047.
49. Takada, A., C. Robison, H. Goto, A. Sanchez, K. G. Murti, M. A. Whitt, and Y. Kawaoka. 1997. A system for functional analysis of Ebola virus glycoprotein. Proc Natl Acad Sci USA. 94:14764-14769.
50. Tong, S., F. Yi, A. Martin, Q. Yao, M. Li, and R. W. Compans. 2001. Three membrane-proximal amino acids in the human parainfluenza type 2 (HPIV 2) F protein are critical for fusogenic activity. Virology. 280:52-61.
51. White, J. M. 1990. Viral and cellular membrane fusion proteins. Annu. Rev. Physiol. 52:675-697.
52. Whitt, M. A., L. Buonocore, J. K. Rose, V. Ciccarone, A. Chytil, and G. Gebeyehu. 1991. TransfectACE Reagent: Transient transfection frequencies greater than 90%. Focus. 13:8-12.
53. Whitt, M. A., P. Zagouras, B. Crise, and J. K. Rose. 1990. A fusion-defective mutant of the vesicular stomatitis virus glycoprotein. J Virol. 64:4907-4913.
54. Zavoritinskaya, T. 1999. Ph.D. Thesis, University of Tennessee Health Science Center.
55. Zhang, L., and H. P. Ghosh. 1994. Characterization of the putative fusogenic domain in vesicular stomatitis virus glycoprotein G. J. Virol. 68:2186-2193.
56. Zhou, J., R. E. Dutch, and R. A. Lamb. 1997. Proper spacing between heptad repeat B and the transmembrane domain boundary of the paramyxovirus SV5 F protein is critical for biological activity. Virology. 239:327-339.

What is claimed is:

1. An isolated nucleic acid sequence, wherein said isolated nucleic acid sequence consists of the nucleic acid sequence that codes for the amino acid sequence set forth in SEQ ID NO: 2,4,5,6,7,8, or 9.

2. An isolated nucleic acid molecule comprising: the isolated nucleic acid sequence of claim 1 and a nucleic acid sequence encoding a fusion facilitating polypeptide.

3. A vector comprising a heterologous nucleic acid sequence that consists of the isolated nucleic acid sequence of claim 2.

4. A cell comprising a heterologous nucleic acid sequence that consists of the isolated nucleic acid sequence of claim 2.

5. A recombinant virus comprising a heterologous nucleic acid sequence that consists of the isolated nucleic acid sequence of claim 2.

6. An isolated nucleic acid molecule, wherein said isolated nucleic acid molecule consists of: (i) the nucleic acid sequence that codes for the amino acid sequence set forth in SEQ ID NO: 2,4,5,6,7, or 8; or (ii) a nucleic acid sequence that is at least 95% identical to the nucleic acid sequence of (i).

7. An isolated nucleic acid molecule consisting of the isolated nucleic acid sequence of claim 6 and a nucleic acid sequence encoding simian virus 5 (SV5) F or HIV envelope protein.

8. A vector comprising a heterologous nucleic acid sequence that consists of the isolated nucleic acid sequence of claim 7.

9. A cell comprising a heterologous nucleic acid sequence that consists of the isolated nucleic acid sequence of claim 7.

10. A recombinant virus comprising a heterologous nucleic acid sequence that consists of the isolated nucleic acid sequence of claim 7.

* * * * *